(12) United States Patent
Cerynik et al.

(10) Patent No.: US 11,389,216 B2
(45) Date of Patent: Jul. 19, 2022

(54) ORTHOPEDIC FIXATION SCREW WITH BIORESORBABLE LAYER

(71) Applicant: Stabiliz Orthopaedics, LLC, Exton, PA (US)

(72) Inventors: Douglas Cerynik, Wynnewood, PA (US); Susan P. Harding, Galloway, NJ (US)

(73) Assignee: Stabiliz Orthopaedics, LLC, Exton, PA (US)

( * ) Notice: Subject to any disclaimer, the term of this patent is extended or adjusted under 35 U.S.C. 154(b) by 515 days.

(21) Appl. No.: 16/373,159

(22) Filed: Apr. 2, 2019

(65) Prior Publication Data

US 2019/0223926 A1 Jul. 25, 2019

Related U.S. Application Data

(63) Continuation of application No. 15/451,521, filed on Mar. 7, 2017, now abandoned, which is a
(Continued)

(51) Int. Cl.
*A61B 17/80* (2006.01)
*A61B 17/86* (2006.01)
(Continued)

(52) U.S. Cl.
CPC .......... *A61B 17/8033* (2013.01); *A61B 17/72* (2013.01); *A61B 17/746* (2013.01);
(Continued)

(58) Field of Classification Search
CPC ... A61B 17/8033; A61B 17/72; A61B 17/746; A61B 17/80; A61B 17/86;
(Continued)

(56) References Cited

U.S. PATENT DOCUMENTS 4,338,926 A 7/1982 Kummer et al.
4,375,810 A 3/1983 Belykh et al.
(Continued)

FOREIGN PATENT DOCUMENTS

CA 2794019 A1 9/2010
DE 43 43 117 A1 6/1995
(Continued)

OTHER PUBLICATIONS

"Large Fragment LCP Instrument and Implant Set. Part of the Synthes locking compression plate (LCP) system," Technique Guide, Synthes, pp. 1-31 (2003).
(Continued)

*Primary Examiner* — Zade Coley
*Assistant Examiner* — Diana Jones
(74) *Attorney, Agent, or Firm* — Schott P.C.

(57) ABSTRACT

The device has a body with holes to accept the bone screws. The bone screws have a layer of bioresorbable material on a surface portion of the head of the screw contiguous with the shaft. Engagement between the bone screws and the body is initially through the bioresorbable material, which engagement rigidly fixes the relative angular orientation between the bone screws and the body when the device is applied to a bone. As the bioresrobable material is resorbed the angular relation between the bone screws and the body is no longer rigidly fixed, thereby effecting a transformation from rigid osteosynthesis to flexible osteosynthesis to allow micromotion between the bone fragments which promotes healing.

18 Claims, 15 Drawing Sheets

Related U.S. Application Data continuation of application No. 14/876,162, filed on Oct. 6, 2015, now Pat. No. 9,622,803, which is a continuation of application No. 13/953,095, filed on Jul. 29, 2013, now Pat. No. 9,179,956, which is a continuation of application No. 12/730,661, filed on Mar. 24, 2010, now Pat. No. 8,506,608.

(60) Provisional application No. 61/162,987, filed on Mar. 24, 2009.

(51) Int. Cl.
  *A61B 17/72* (2006.01)
  *A61B 17/74* (2006.01)
  *A61B 17/00* (2006.01)

(52) U.S. Cl.
  CPC .............. *A61B 17/80* (2013.01); *A61B 17/86* (2013.01); *A61B 17/8605* (2013.01); *A61B 17/866* (2013.01); *A61B 17/8625* (2013.01); *A61B 17/8047* (2013.01); *A61B 17/864* (2013.01); *A61B 2017/00004* (2013.01)

(58) Field of Classification Search
  CPC ........ A61B 17/8605; A61B 2017/8655; A61B 17/866; A61B 17/8047; A61B 17/864; A61B 2017/0004
  See application file for complete search history.

(56) References Cited

U.S. PATENT DOCUMENTS

| | | |
|---|---|---|
| 4,524,765 A | 6/1985 | de Zbikowski |
| 4,550,723 A | 11/1985 | Belykh et al. |
| 4,773,406 A | 9/1988 | Spector et al. |
| 4,838,252 A | 6/1989 | Klaue |
| 4,905,680 A | 3/1990 | Tunc |
| 4,943,292 A | 7/1990 | Foux |
| 4,973,333 A | 11/1990 | Treharne |
| 5,002,544 A | 3/1991 | Klaue et al. |
| 5,013,315 A | 5/1991 | Barrows |
| 5,057,111 A | 10/1991 | Park |
| 5,084,051 A | 1/1992 | Törmälä et al. |
| 5,098,434 A | 3/1992 | Serbousek |
| 5,108,399 A | 4/1992 | Eitenmuller et al. |
| 5,258,044 A | 11/1993 | Lee |
| 5,275,601 A | 1/1994 | Gogolewski et al. |
| 5,360,448 A | 11/1994 | Thramann |
| 5,360,452 A | 11/1994 | Engelhardt et al. |
| 5,368,593 A | 11/1994 | Stark |
| 5,505,736 A | 4/1996 | Reimels et al. |
| 5,571,139 A | 11/1996 | Jenkins, Jr. |
| 5,578,034 A | 11/1996 | Estes |
| 5,643,269 A | 7/1997 | Härle |
| 5,709,686 A | 1/1998 | Talos et al. |
| 5,711,763 A | 1/1998 | Nonami et al. |
| 5,733,287 A | 3/1998 | Tepic et al. |
| 5,741,258 A | 4/1998 | Klaue et al. |
| 5,785,712 A | 7/1998 | Runciman et al. |
| 5,797,912 A | 8/1998 | Runciman et al. |
| 5,954,722 A | 9/1999 | Bono |
| 5,997,541 A | 12/1999 | Schenk |
| 6,001,099 A | 12/1999 | Huebner |
| 6,004,323 A | 12/1999 | Park et al. |
| 6,086,060 A | 7/2000 | Berthold |
| 6,206,881 B1 | 3/2001 | Frigg et al. |
| 6,248,108 B1 | 6/2001 | Törmälä et al. |
| 6,309,393 B1 | 10/2001 | Tepic et al. |
| 6,471,707 B1 | 10/2002 | Miller et al. |
| 6,510,751 B2 | 1/2003 | Giometti |
| 6,527,776 B1 | 3/2003 | Michelson |
| 6,540,746 B1 | 4/2003 | Bühler et al. |
| 6,547,792 B1 | 4/2003 | Tsuji et al. |
| 6,620,163 B1 | 9/2003 | Michelson |
| 6,623,486 B1 | 9/2003 | Weaver et al. |
| 6,666,868 B2 | 12/2003 | Fallin |
| 6,679,883 B2 | 1/2004 | Hawkes et al. |
| 6,716,957 B2 | 4/2004 | Tunc |
| 6,719,759 B2 | 4/2004 | Wagner et al. |
| 6,747,121 B2 | 6/2004 | Gogolewski |
| 6,821,278 B2 | 11/2004 | Frigg et al. |
| 6,890,334 B2 | 5/2005 | Brace et al. |
| 6,893,443 B2 | 5/2005 | Frigg et al. |
| 6,893,444 B2 | 5/2005 | Orbay |
| 6,916,321 B2 | 7/2005 | TenHuisen et al. |
| 6,969,390 B2 | 11/2005 | Michelson |
| 6,991,802 B1 | 1/2006 | Ahola et al. |
| 6,998,134 B2 | 2/2006 | Schmidmaier et al. |
| 7,128,744 B2 | 10/2006 | Weaver et al. |
| 7,169,150 B2 | 1/2007 | Shipp et al. |
| 7,175,624 B2 * | 2/2007 | Konieczynski .... A61B 17/7059 606/288 |
| 7,179,260 B2 | 2/2007 | Gerlach et al. |
| 7,235,079 B2 | 6/2007 | Jensen et al. |
| 7,250,053 B2 | 7/2007 | Orbay |
| 7,270,665 B2 | 9/2007 | Morrison et al. |
| 7,276,070 B2 | 10/2007 | Mückter |
| 7,309,340 B2 | 12/2007 | Fallin et al. |
| 7,311,712 B2 | 12/2007 | Dalton |
| 7,341,589 B2 | 3/2008 | Weaver et al. |
| 7,354,441 B2 | 4/2008 | Frigg |
| 7,524,891 B2 | 4/2009 | Rose et al. |
| 7,537,596 B2 | 5/2009 | Jensen |
| 7,905,910 B2 | 3/2011 | Gerlach et al. |
| 7,976,570 B2 | 7/2011 | Wagner et al. |
| 8,309,521 B2 | 11/2012 | Zhang et al. |
| 8,506,608 B2 | 8/2013 | Cerynik et al. |
| 9,125,699 B2 | 9/2015 | Zahrly et al. |
| 9,179,956 B2 | 11/2015 | Cerynik et al. |
| 9,622,803 B2 | 4/2017 | Cerynik et al. |
| 2002/0077631 A1 | 6/2002 | Lubbers et al. |
| 2003/0149436 A1 | 8/2003 | McDowell et al. |
| 2005/0113834 A1 | 5/2005 | Breitenstien et al. |
| 2006/0095039 A1 | 5/2006 | Mutchler |
| 2006/0095040 A1 | 5/2006 | Schlienger et al. |
| 2006/0142765 A9 | 6/2006 | Dixon et al. |
| 2006/0149262 A1 * | 7/2006 | Branemark .......... A61C 8/0033 606/301 |
| 2006/0235518 A1 | 10/2006 | Blain |
| 2007/0055244 A1 | 3/2007 | Jackson |
| 2007/0055251 A1 | 3/2007 | Huebner et al. |
| 2007/0191848 A1 | 8/2007 | Wack et al. |
| 2007/0276405 A1 | 11/2007 | Huebner et al. |
| 2007/0292820 A1 | 12/2007 | Canter |
| 2008/0177330 A1 | 7/2008 | Ralph et al. |
| 2008/0188899 A1 | 8/2008 | Bottlang et al. |
| 2008/0269807 A1 | 10/2008 | Simon et al. |
| 2009/0036893 A1 | 2/2009 | Kartalian et al. |
| 2009/0082814 A1 * | 3/2009 | Bickley .............. A61B 17/686 606/286 |
| 2010/0042215 A1 | 2/2010 | Stalcup et al. |
| 2014/0058461 A1 * | 2/2014 | Black .................. A61B 17/864 606/314 |
| 2017/0172635 A1 | 6/2017 | Cerynik et al. |

FOREIGN PATENT DOCUMENTS

| | | |
|---|---|---|
| EP | 2 005 978 A1 | 12/2008 |
| JP | H07-184921 A | 7/1995 |
| JP | H07-213534 A | 8/1995 |
| JP | H10-14935 A | 1/1998 |
| JP | 2000-515396 A | 11/2000 |
| JP | 2002-525157 A | 8/2002 |
| JP | 2005-205214 A | 8/2005 |
| JP | 2005-527255 A | 9/2005 |
| JP | 2007-510483 A | 4/2007 |
| JP | 2007-522846 A | 8/2007 |
| JP | 2009-011825 A | 1/2009 |
| JP | 2009-501575 A | 1/2009 |
| JP | 2009-511170 A | 3/2009 |
| JP | 2009-527261 A | 7/2009 |
| JP | 2010-517673 A | 5/2010 |

(56) References Cited

FOREIGN PATENT DOCUMENTS

| JP | 2012-521800 A | 9/2012 |
|---|---|---|
| JP | 2014-237026 A | 12/2014 |
| JP | 2016-195837 A | 11/2016 |
| WO | 97/25930 A1 | 7/1997 |
| WO | 00/18309 A1 | 4/2000 |
| WO | 03/037169 A2 | 5/2003 |
| WO | 2007/009124 A2 | 1/2007 |
| WO | 2007/086832 A2 | 8/2007 |
| WO | 2008/051707 A2 | 5/2008 |
| WO | 2008/097403 A1 | 8/2008 |
| WO | 2010/111350 A1 | 9/2010 |

OTHER PUBLICATIONS

"4.5mm LCP™ Condylar Plates," Technique Guide, Synthes, pp. 1-35 (2002).

Hollinger, J.O., and Bai Iistone, GC., "Biodegradable Bone Repair Materials: Synthetic Polymers and Ceramics," Army Institute of Dental Research, Report date Jan. 1985, accessed at http://www.dtic.mil/docs/citations/ADA154756, accessed on Jul. 10, 2018, pp. 1-60.

Extended European Search Report dated Oct. 10, 2014, as received in Application No. 10756765.3.

International Search Report and Written Opinion of International Searching Authority for PCT Application No. PCT/US201 0/028437 dated May 17, 2010.

* cited by examiner

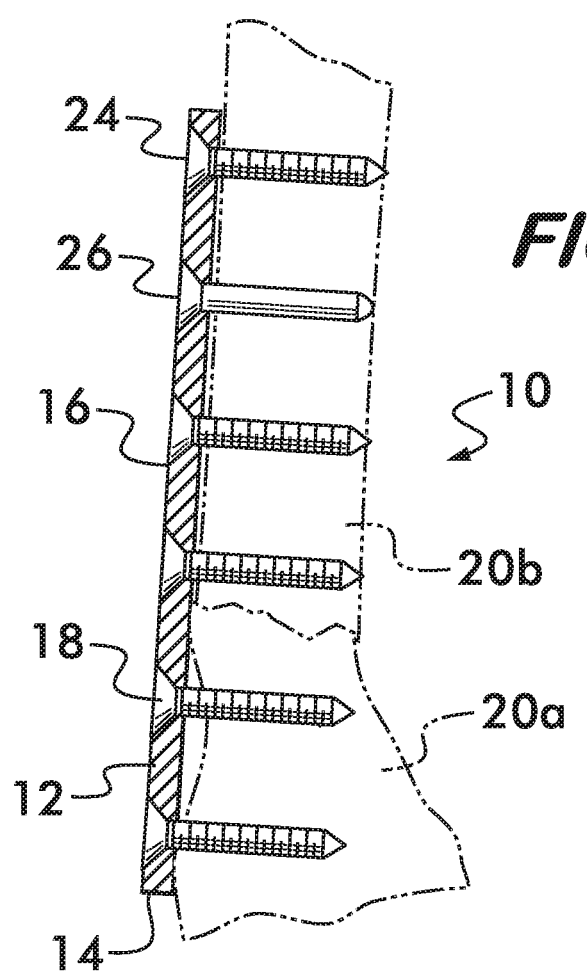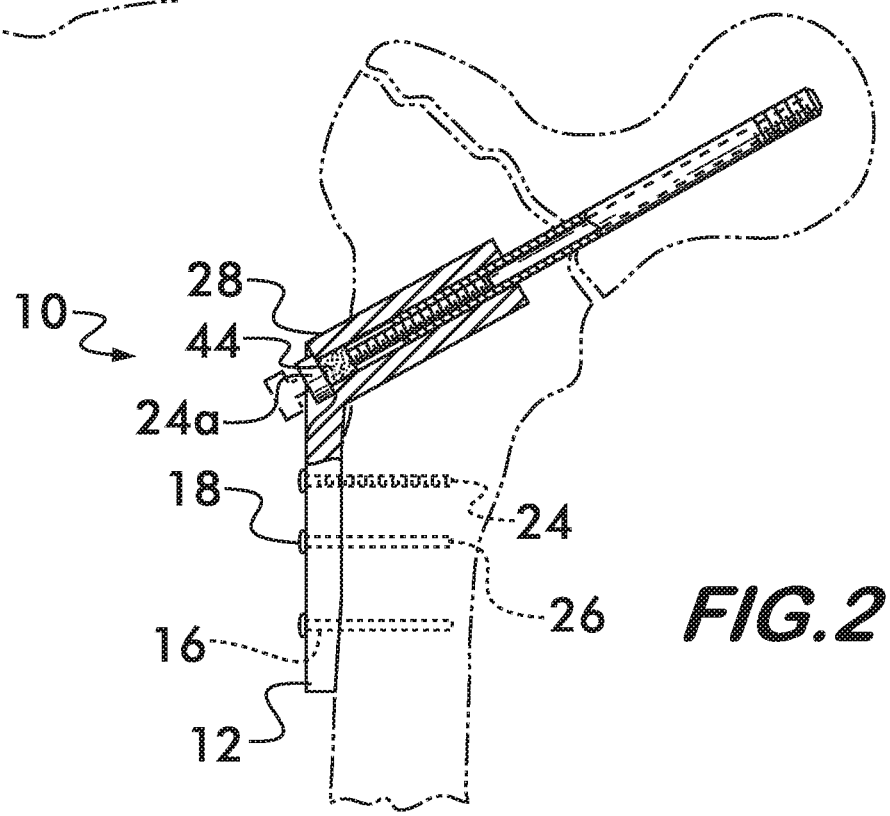

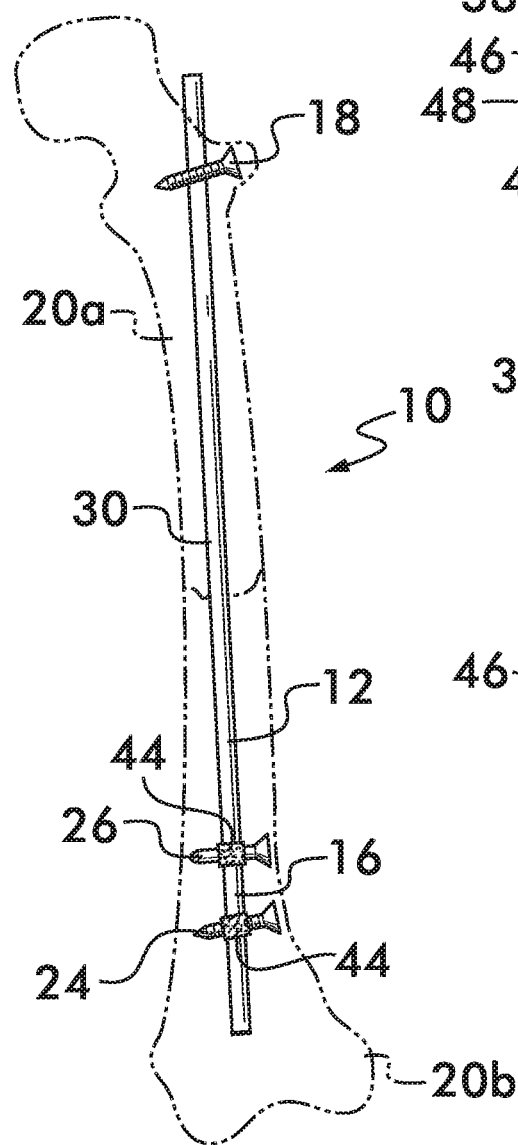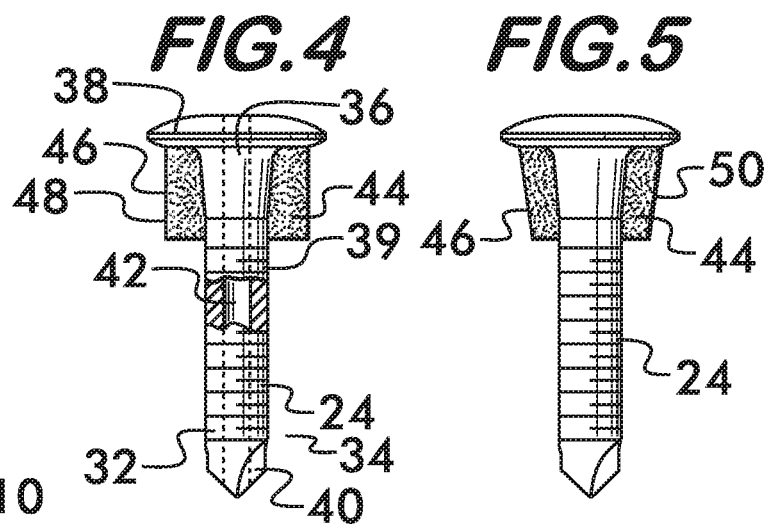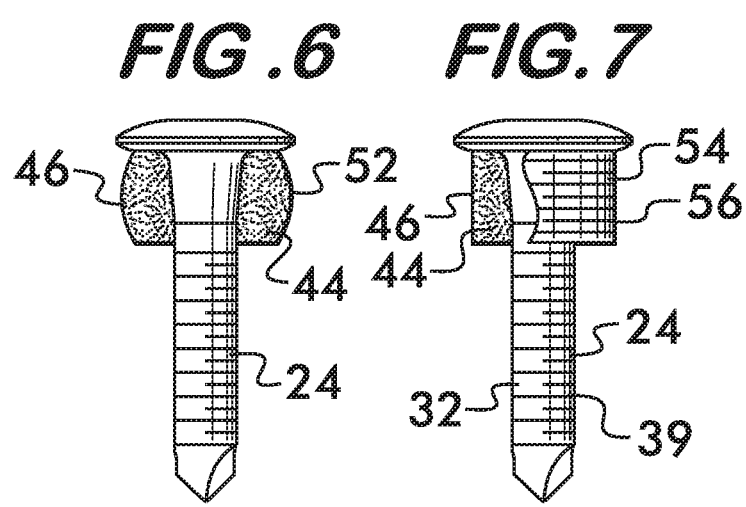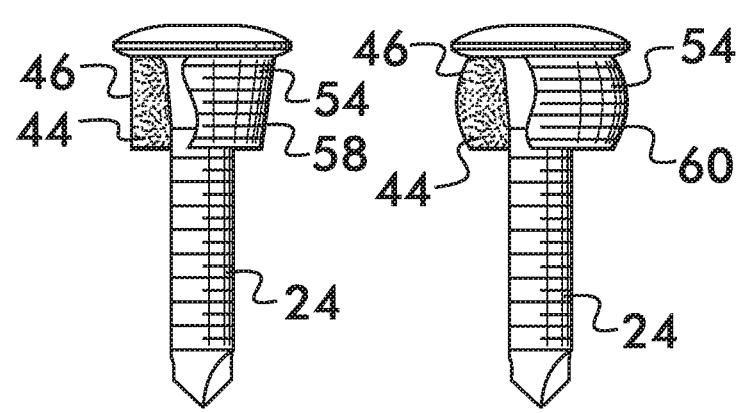

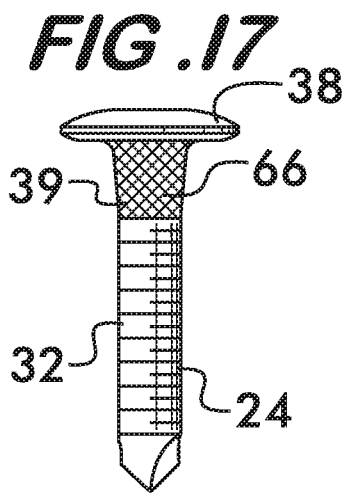
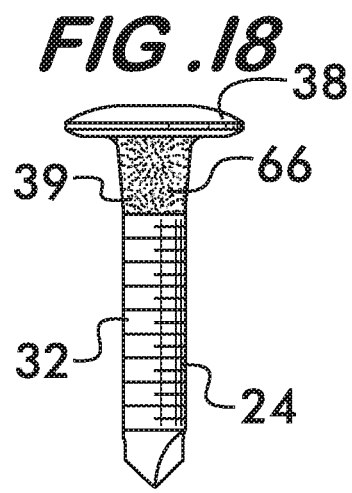
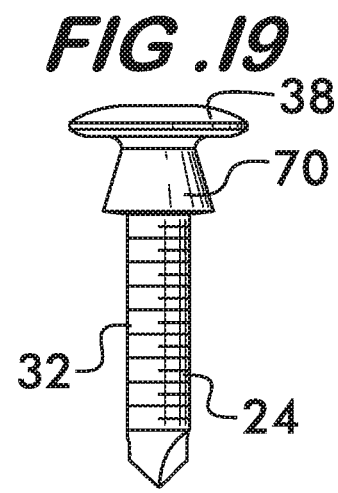
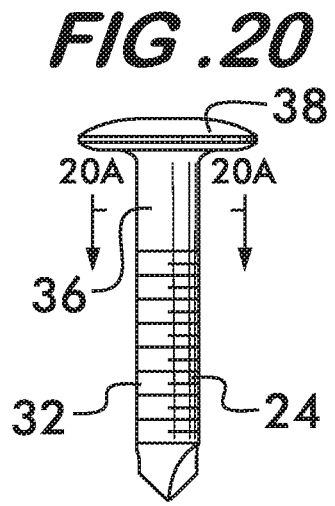
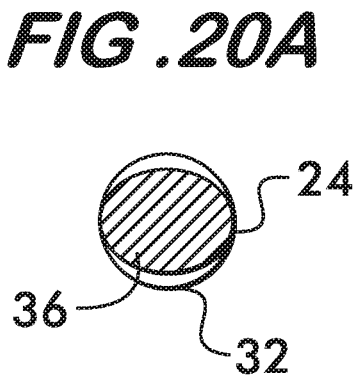
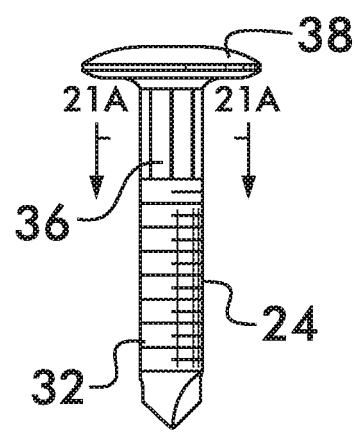
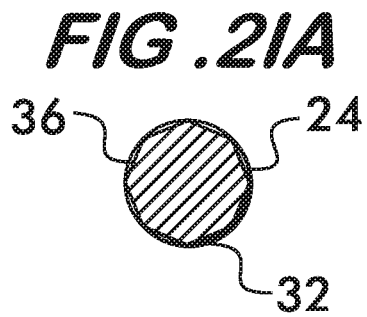
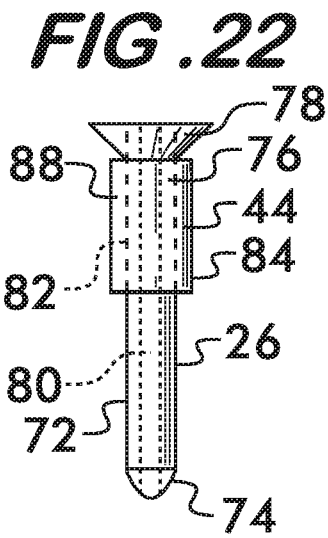

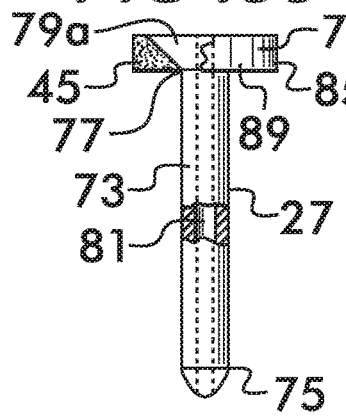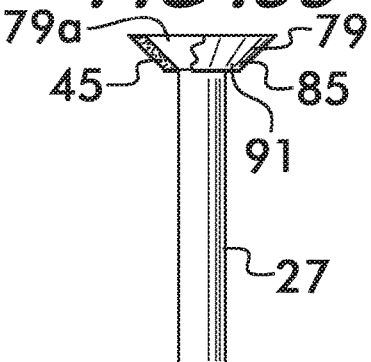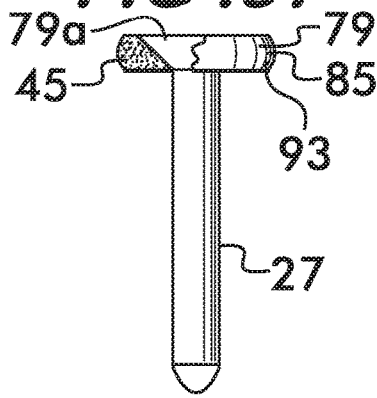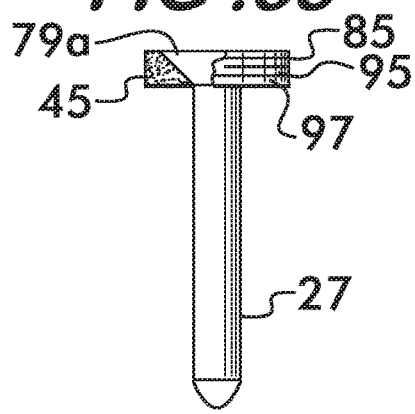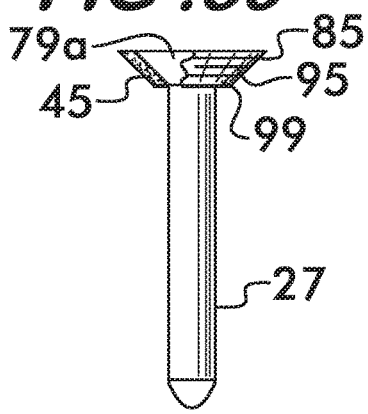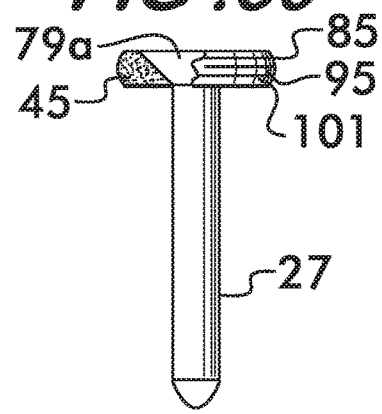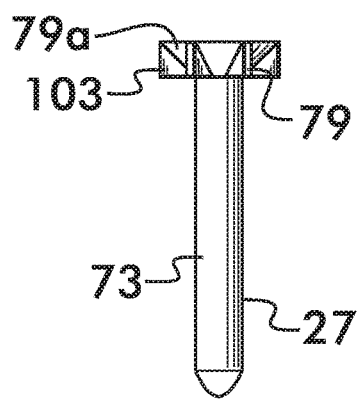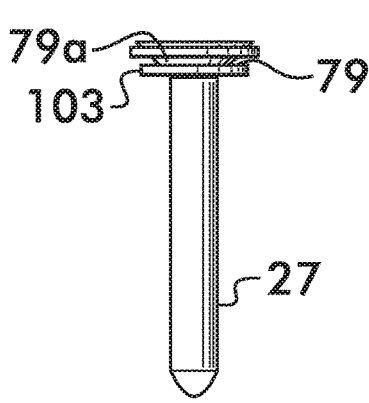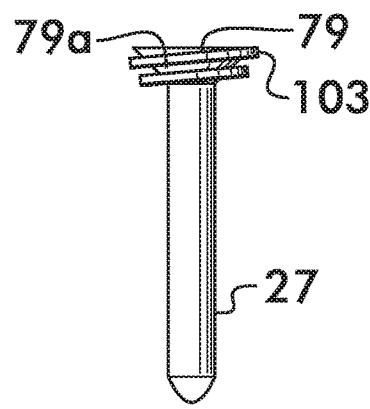

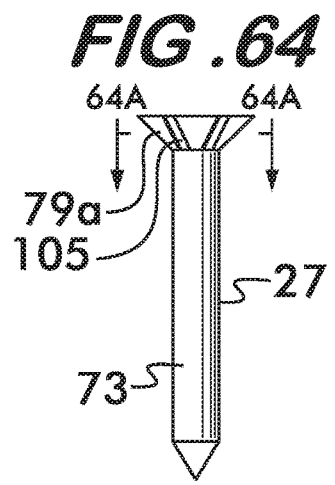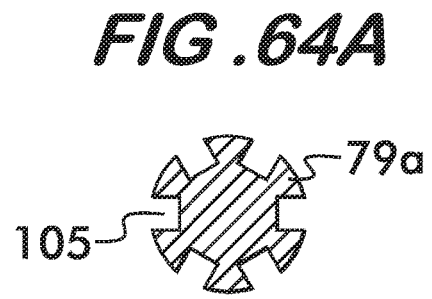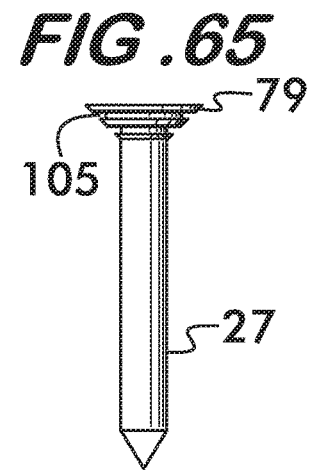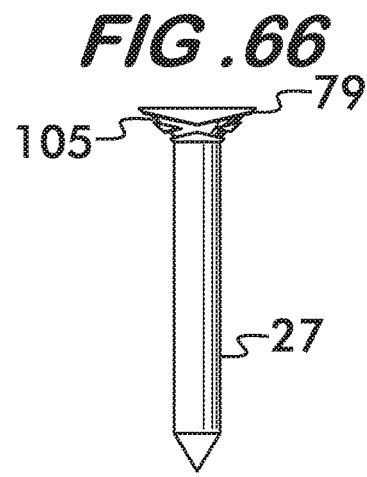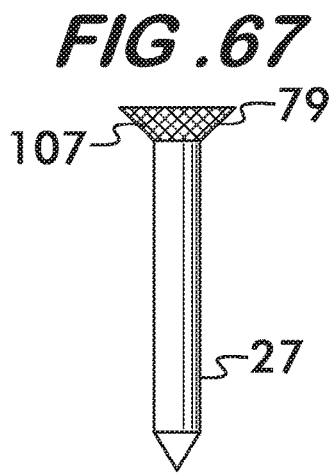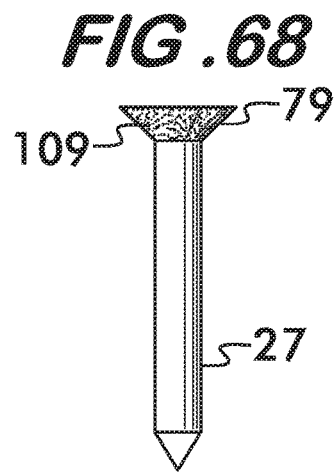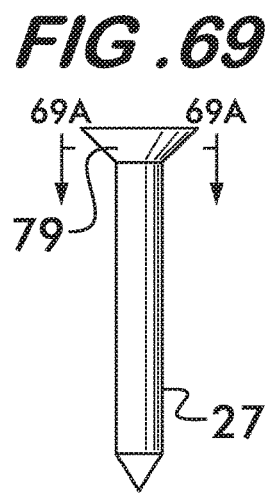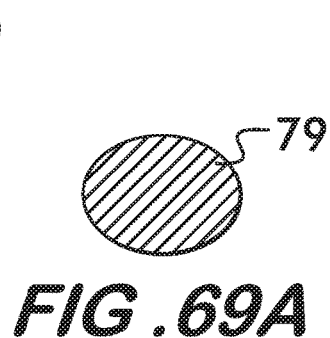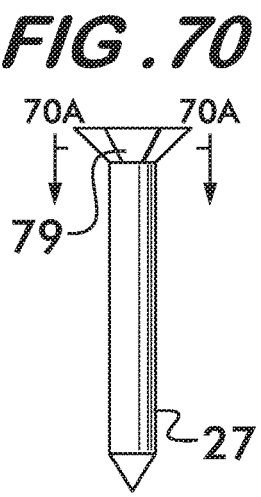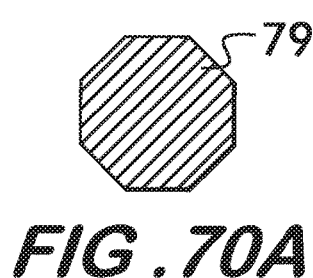

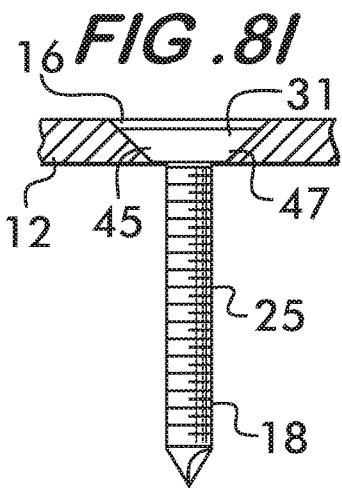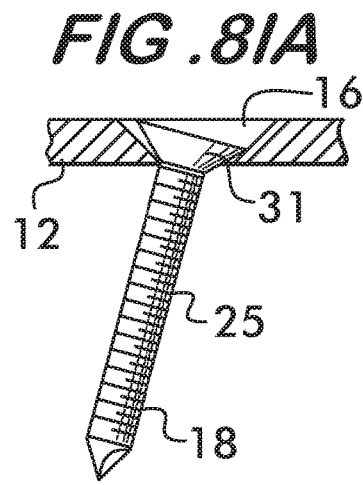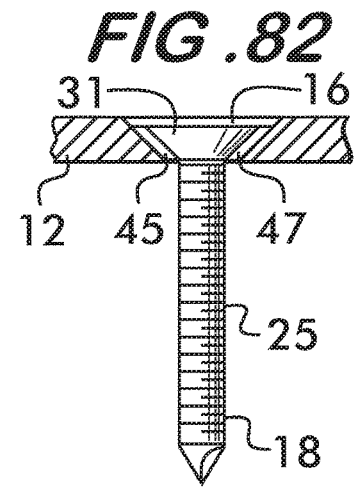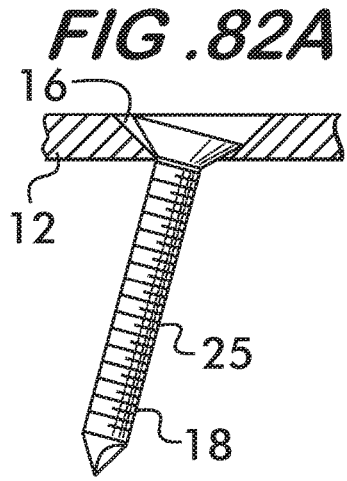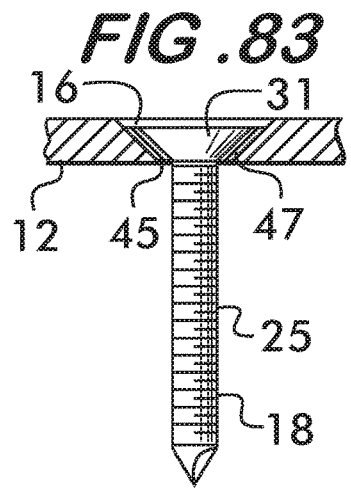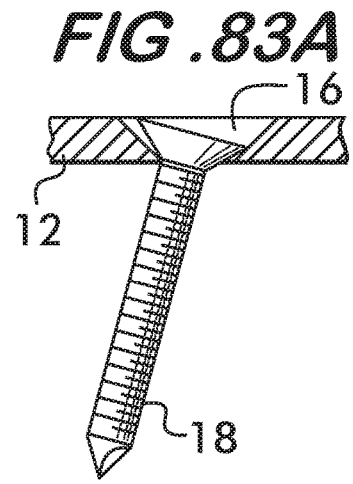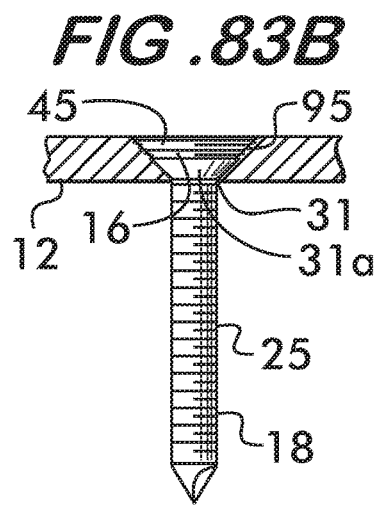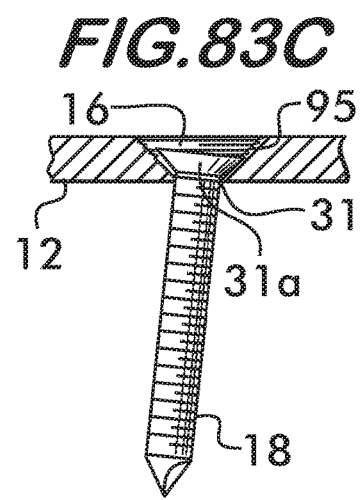

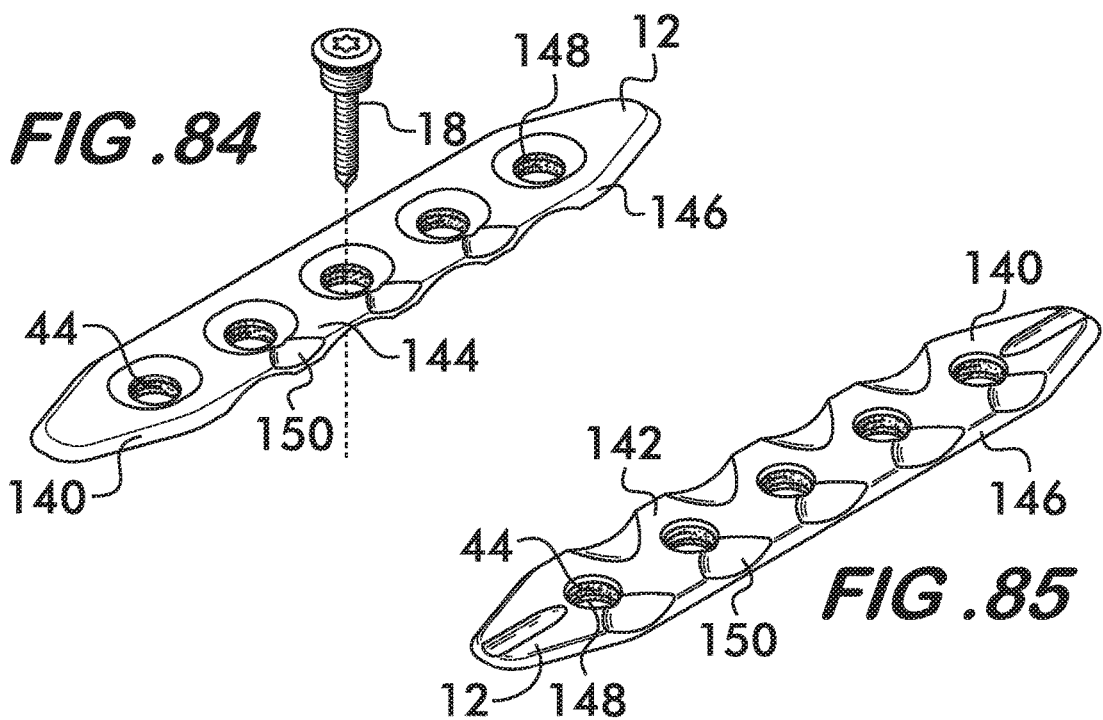
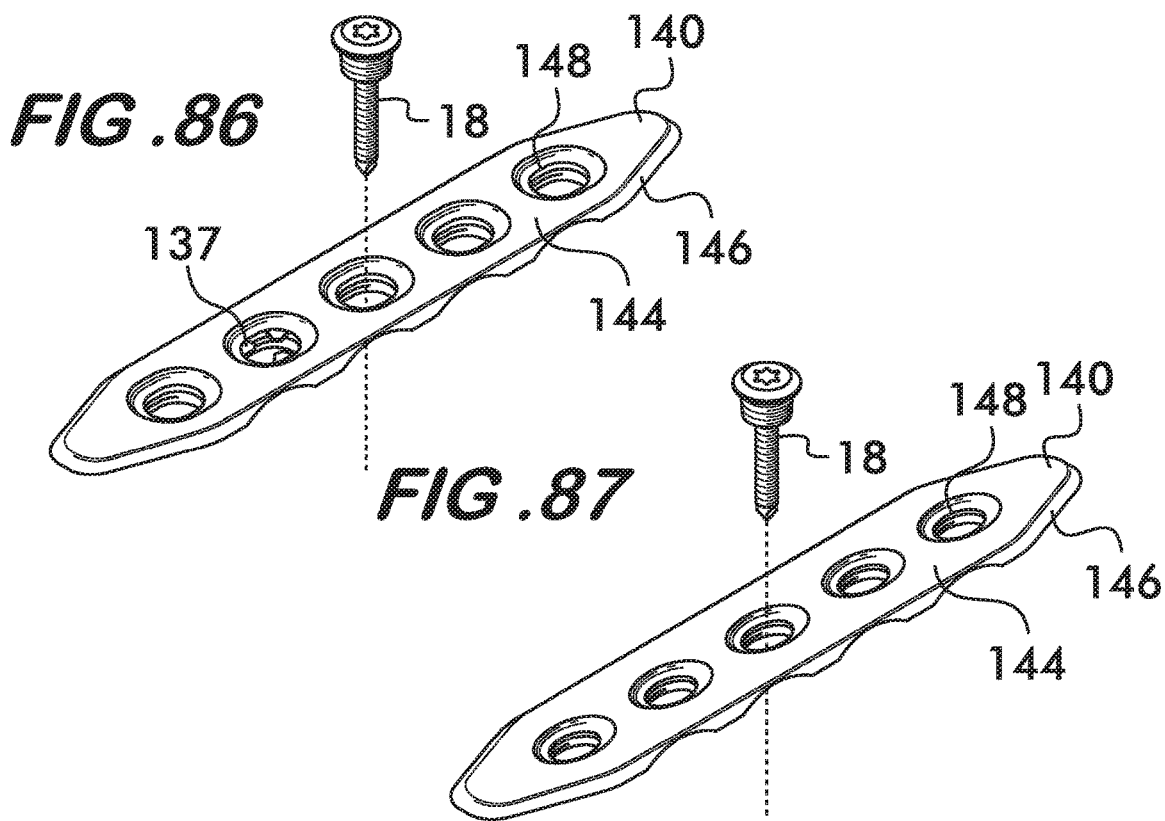

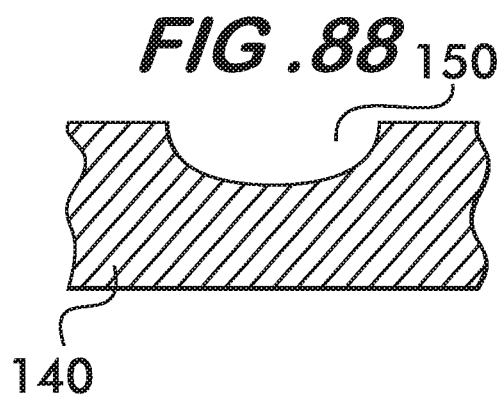
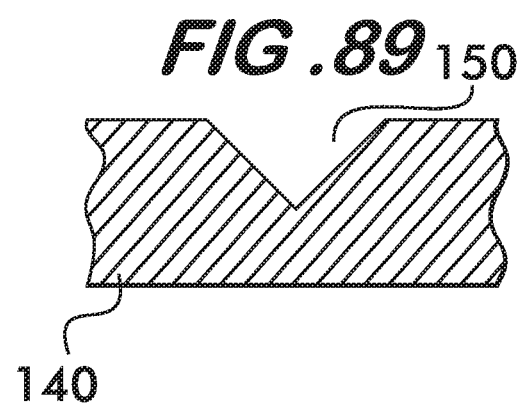
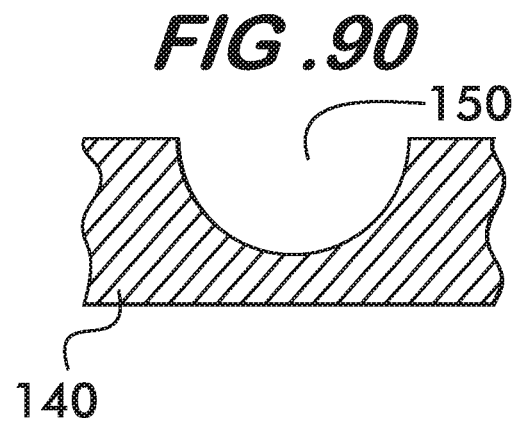
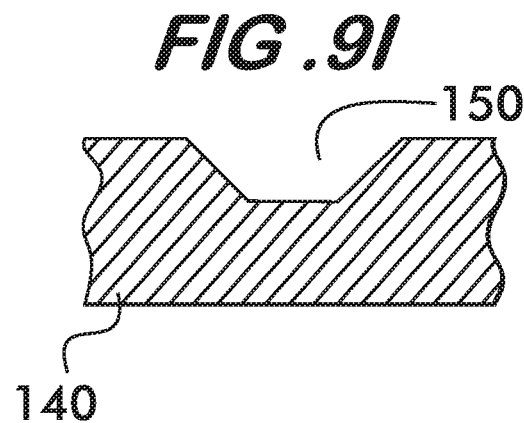
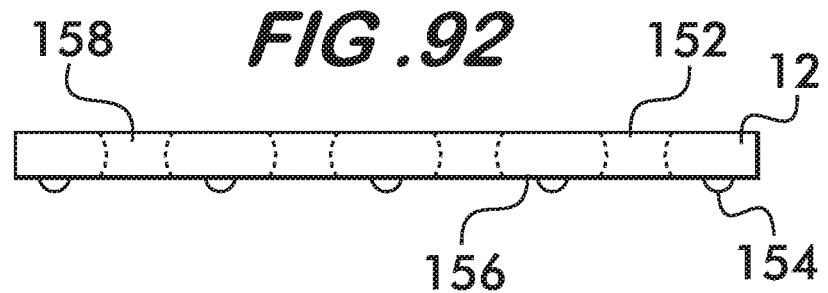

ORTHOPEDIC FIXATION SCREW WITH BIORESORBABLE LAYER

CROSS REFERENCE TO RELATED APPLICATIONS

This application is a continuation of and claims priority to U.S. patent application Ser. No. 15/451,521 filed Mar. 7, 2017, which is a continuation of Ser. No. 14/876,162, filed Oct. 6, 2016, now U.S. Pat. No. 9,622,803 issued Apr. 18, 2017, which is a continuation of U.S. patent application Ser. No. 13/953,095, filed Jul. 29, 2013, now U.S. Pat. No. 9,179,956 issued Nov. 10, 2015, which is a continuation of U.S. patent application Ser. No. 12/730,661, filed Mar. 24, 2010, now U.S. Pat. No. 8,506,608, issued Aug. 13, 2013, which patent claims priority to U.S. Provisional Application No. 61/162,987 filed Mar. 24, 2009, the applications all being hereby incorporated by reference herein.

FIELD OF THE INVENTION

This invention relates to screws used with fixation devices for the treatment of bone fractures using flexible and rigid osteosynthesis.

BACKGROUND

The clinical success of plate and screw systems for internal fixation of fractures is well-documented. Current systems offer the surgeon a choice of conventional plates and screws, locking plates and screws, or various types of combination plates and screws.

Conventional bone plates and screws may be used for treating fractures involving severely comminuted bone or missing bone segments. These conventional systems may also be described as "flexible osteosynthesis" or "biological osteosynthesis" and are particularly well-suited to promoting healing of the fracture by compressing the fracture ends together and drawing the bone into close apposition with other fragments and the bone plate. They are particularly useful in the treatment of comminuted fractures in the diaphyseal region of bones or in regions with severe segmental bone loss. In the case of these fractures, it is imperative to maintain proper bone length while correcting fracture fragments for proper anatomic alignment. With flexible osteosynthesis, the fracture zone is not directly affixed or manipulated, and consequently, the blood circulation in this area is not inhibited.

Bone plates designed for flexible osteosynthesis thus operate similarly to a locking, intramedullary nail, which is anchored only in the metaphyses. Flexible osteosynthesis repair constructs allow for micromotion across the fracture site stimulating callous formation. Since the angular relationships between the plate and screws are not fixed, they can change postoperatively, leading to mal-alignment and poor clinical results.

The primary mechanism for the change in angular relationship is related to energy storage. Threading a bone screw into bone compresses the bone against the plate. The compression results in high strain in the bone, and, consequently, energy storage. With the dynamic loading resulting from physiological conditions, loosening of the plate and screw and loss of the stored energy can result.

Conventional bone screws, i.e. screws that are not secured to a plate so that a fixed angular relationship between the plate and screw is maintained (hereinafter "non-locking screws") effectively compress bone fragments, but possess a low resistance to shear force that can lead to loosening of the screw.

The development of plates incorporating a fixed angular relationship between the bone plate and screws have been developed to combat this problem. Methods of securing the screw to the plate are known as so-called "locking plates", "locking screws" or "rigid osteosynthesis". This type of fixation is particularly useful in treating peri-articular fractures, simple shaft fractures (where nailing is impossible), as well as osteotomies. Aside from the possibility of anatomical repositioning, the bone itself supports and stabilizes the osteosynthesis, which allows for the possibility of putting stress on the extremity earlier and without pain.

Securing the screw in a fixed angle to the plate reduces the incidence of loosening. As the relationship between the locking screws and the plate is fixed, locking screws provide a high resistance to shear or torsional forces.

However, locking screws have a limited capability to compress bone fragments. Additionally, locking screws hold the construct in such a rigid position that micromotion across the fracture site may be impeded thereby inhibiting callous formation. Though used successfully for certain fractures, rigid osteosynthesis has been shown to promote the occurrence of non-unions at the fracture site.

A locking screw has threading on an outer surface of its head that mates with corresponding threading on the surface of a plate hole to lock the screw to the plate. Bone plates having threaded holes for accommodating locking screws are known. For example, German Patent Application No. 43 43 117 discloses a bone plate with threaded holes for locking screws.

Locking screws have a high resistance to shear force that ensure stability at the bone screw/plate hole interface, but possess a limited ability to compress bone fragments.

Since fractures cannot always be treated with both types of osteosynthesis at the same fixation point, surgeons must frequently compromise because bone plate screw holes only allow him to choose between one of these two types of continuous osteosynthesis discussed above. The ideal fracture stabilization construct would allow the surgeon to choose between continuous flexible osteosynthesis, continuous rigid osteosynthesis and temporary rigid osteosynthesis transforming to flexible osteosynthesis within a pre-defined time period.

By having the option to rigidly fix a fracture fragment via a known location for a pre-determined period of time and allowing that rigid fixation to transform into a region of flexible osteosynthesis, the surgeon is thus enabled to expose the fracture site to a period of stability followed by controlled micromotion thus stimulating bony healing.

SUMMARY

The invention concerns an orthopedic fixation device for connecting a first bone portion to a second bone portion. The device comprises a body for linking the first bone portion to the second bone portion. The body has a plurality of holes extending therethrough. A screw is insertable though at least one of the holes extending through the body. The screw comprises a shaft having a distal end and an oppositely disposed proximal end. External helical screw threads extend along at least a first portion of the shaft. A head is attached to the proximal end of the shaft. A layer of bioresorbable material is positioned surrounding a second portion of the shaft, either adjacent to the head or in spaced relation to the head. The layer of bioresorbable material has an outer surface engageable with the body to initially fix the screw at a desired angular position relatively to the body.

The screw is angularly movable with respect to the body upon resorbtion of at least a portion of the bioresorbable layer.

In another embodiment, an orthopedic fixation device for connecting a first bone portion to a second bone portion according to the invention comprises a body for linking the first bone portion to the second bone portion. The body has a plurality of holes extending therethrough. A layer of bioresorbable material is positioned on the body within at least one of the holes. A screw is insertable though the at least one hole. The screw comprises a shaft having a distal end and an oppositely disposed proximal end. External helical screw threads extend along at least a first portion of the shaft. A head is attached to the proximal end of the shaft. A second portion of the shaft, adjacent to the head, or in spaced relation to the head, is engageable with the bioresorbable layer to initially fix the screw at a desired angular position relatively to the body. The screw is angularly movable with respect to the body upon resorbtion of at least a portion of the bioresorbable layer.

In another embodiment of an orthopedic fixation device for connecting a first bone portion to a second bone portion, the device comprises a body for linking the first bone portion to the second bone portion. The body has a plurality of holes extending therethrough.

A screw is insertable though at least one of the holes extending through the body. The screw comprises a shaft having a distal end and an oppositely disposed proximal end. External helical screw threads extending along at least a first portion of the shaft. A head is attached to the proximal end of the shaft. The head has a surface portion contiguous with the proximal end of the shaft. A layer of bioresorbable material is positioned on the surface portion of the head contiguous with the proximal end of the shaft. The layer of bioresorbable material has an outer surface engageable with the body to initially fix the screw at a desired angular position relatively to the body. The screw is angularly movable with respect to the body upon resorbtion of at least a portion of the bioresorbable layer.

In another embodiment of an orthopedic fixation device for connecting a first bone portion to a second bone portion according to the invention, the device comprises a body for linking the first bone portion to the second bone portion. The body has a plurality of holes extending therethrough.

A layer of bioresorbable material is positioned on the body within at least one of the holes. A screw is insertable though the at least one hole. The screw comprises a shaft having a distal end and an oppositely disposed proximal end. External helical screw threads extend along at least a first portion of the shaft. A head is attached to the proximal end of the shaft. The head has a surface portion contiguous with the proximal end of the shaft. The surface portion contiguous with the proximal end of the shaft is engageable with the bioresorbable layer to initially fix the screw at a desired angular position relatively to the body. The screw is angularly movable with respect to the body upon resorbtion of at least a portion of the bioresorbable layer.

Another orthopedic fixation device for connecting a first bone portion to a second bone portion comprises a body having a bone contacting surface and an obverse surface arranged opposite to the bone contacting surface. A side surface extends between the bone contacting surface and the obverse surface. A plurality of holes extending through the body. At least one channel is positioned within either or both the obverse surface and the bone contacting surface and extends from one of the holes to the side surface.

Another embodiment of an orthopedic fixation device for connecting a first bone portion to a second bone portion comprises a body having a bone facing surface, an obverse surface arranged opposite to the bone facing surface, and a plurality of holes extending through the body between the bone facing surface and the obverse surface. A plurality of projections are positioned on the bone facing surface and extend outwardly away therefrom.

Another orthopedic fixation device for connecting a first bone portion to a second bone portion according to the invention comprises a body for linking the first bone portion to the second bone portion. The body has a plurality of holes extending therethrough.

A fastener is insertable though at least one of the holes extending through the body. The fastener comprises a shaft having a distal end and an oppositely disposed proximal end. A head is attached to the proximal end of the shaft. A layer of bioresorbable material is positioned surrounding a portion of the shaft, adjacent to the head, or in spaced relation to the head. The layer of bioresorbable material has an outer surface engageable with the body to initially fix the fastener at a desired angular position relatively to the body. The fastener is angularly movable with respect to the body upon resorbtion of at least a portion of the bioresorbable layer.

Another embodiment of an orthopedic fixation device for connecting a first bone portion to a second bone portion according to the invention comprises a body for linking the first bone portion to the second bone portion. The body has a plurality of holes extending therethrough.

A fastener is insertable though at least one of the holes extending through the body. The fastener comprises a shaft having a distal end and an oppositely disposed proximal end. A head is attached to the proximal end of the shaft. The head has a surface portion contiguous with the proximal end of the shaft. A layer of bioresorbable material is positioned on the surface portion of the head contiguous with the proximal end of the shaft. The layer of bioresorbable material has an outer surface engageable with the body to initially fix the fastener at a desired angular position relatively to the body. The fastener is angularly movable with respect to the body upon resorbtion of at least a portion of the bioresorbable layer.

In the example embodiments described the bioresorbable material is selected form the group consisting of polylactic acid (PLA), poly-L-lactic-co-glycolic acid (PLGA), poly-D/L-lactic acid with or without polyglycolic acid (PDLLA, PDLLA-co-PGA), poly-L-lactic acid with or without -tricalcium phosphate (PLLA, PLLA-TCP), poly-L-lactic acid with hydroxyapatite (PLLA-HA), polycaprolactone (PCL), polycaprolactone-Calcium Phosphate (PCL-CaP), poly(L-lactide-co-D,L-lactide) (PLADLA), hydroxyapatite (HA), tricalcium phosphate m-TCP), nanodiamond particles (ND) and combinations thereof. Another example includes bioresorbable material that expand upon contact with bodily fluids. In a specific example embodiment, the bioresorbable material is selected form the group consisting of copolymer lactic glycolic acid, biodegradeable self-expanding poly-L, D-lactide, PDLLA comprising D-Lactide and L-lactide and poly-L-lactide and poly-E-caprolactone homopolymers, methylmelhacrylate and acrylic acid and cross linking agent allymelhacrylate, and combinations thereof.

The invention also encompasses a method of treating a bone fracture in a living organism having a plurality of bone fragments. The method comprises:

attaching a body to at least two of the bone fragments using a plurality of fasteners joining the body to the fragments;

fixing an angular orientation of at least one of the fasteners in relation to the body using a bioresorbable material positioned between the fastener and the body, the bioresorbable material contacting the one fastener and the body and preventing relative rotation therebetween;

allowing the bioresorbable material to be resorbed by the living organism, thereby allowing relative rotation between the one fastener and the body.

BRIEF DESCRIPTION OF THE DRAWINGS

FIG. 1 is a longitudinal sectional view of a bone plate fixation system;

FIG. 2 is a longitudinal sectional view of a hip screw fixation system;

FIG. 3 is an elevational view of an intramedullary rod fixation system;

FIGS. 4-9 are partial sectional views of bone screws having a layer of bioresorbable material thereon;

FIGS. 10, 11, 11A, 12-14, 14A, 15-20, 20A, 21 and 21A are detailed elevational views of bone screws having features for facilitating attachment of a layer of bioresorbable material thereto;

FIGS. 22-27 are elevational views of pins having a layer of bioresorbable material thereon;

FIGS. 55-60 are elevational views of pins having a layer of bioresorbable material thereon;

FIGS. 61-64, 64A, 65-69, 69A, 70 and 70A are elevational views of pins having features for facilitating attachment of a layer of bioresorbable material thereto;

FIGS. 78, 78A, 79, 79A, 80, 80A, 81, 81A, 82, 82A, 83, 83A, 83B and 83C are partial sectional views of a portion of a fixation device illustrating rigid to flexible osteosynthesis transformation;

FIGS. 84 and 85 are isometric views of an example bone plate embodiment;

FIGS. 86 and 87 are partial isometric views of example embodiments of bone plate details;

FIGS. 88-91 are cross sectional views showing different embodiments of the bone plate shown in FIGS. 84-87; and FIG. 92 is an elevational view of an alternate embodiment of a bone plate according to the invention.

DETAILED DESCRIPTION

Figure 10:
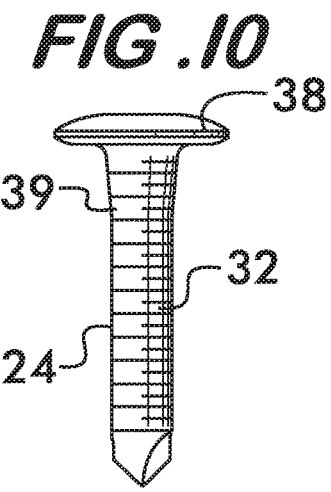

FIGS. 1 through 3 illustrate example orthopedic fixation devices 10 according to the invention. FIG. 1 shows device 10 having a body 12, in this example, a bone plate 14. Bone plate 14 has a plurality of holes 16 which receive fasteners 18 for attaching the bone plate 14 to bone portions 20a and 20b for the repair of a fracture 22. Example fasteners 18 include bone screws 24, and pins 26. The example orthopedic fixation device 10 in FIG. 2 is a hip screw 28, the hip screw comprising a body 12 having holes 16 which receive fasteners 18. Again, the fasteners include bone screws 24 and pins 26 as well as other components such as compressing screw 24a.

FIG. 3 illustrates an intramedullary rod 30, the rod comprising a body 12 having holes 16 to receive fasteners 18, such as bone screws 24 and or pins 26 for attachment of the rod to bone portions 20a and 20b. The body, screws and pins are made of biocompatible materials such as stainless steel and titanium.

These three orthopedic fixation devices are illustrative examples of the invention disclosed herein, but are not meant to limit application of the invention, it being understood that the detailed descriptions of the various components which follow apply to the devices disclosed herein as well as similar devices used for orthopedic fixation in the treatment of bone fractures as well as other disorders. For example, the invention may be used in spinal fixation systems, in particular, to anterior cervical plating systems.

FIG. 4 shows an example bone screw 24, comprising a shaft 32, the shaft having a distal end 34 and an oppositely disposed proximal end 36 to which a head 38 is attached. Shaft 32 has external helical screw threads 39 extending along at least a portion of the shaft. Cutting flutes 40 may be positioned at the distal end 34 of the shaft 32, and the screw 24 may be cannulated, having a duct 42 therethrough. In this embodiment, a layer of bioresorbable material 44 is positioned surrounding a portion of the shaft 32 adjacent to the head 38. The layer of bioresorbable material may be formed on the shaft 32 by injection molding techniques for example. The layer of bioresorbable material 44 has an outer surface 46 which is engageable with the body 12 of the device 10 (see FIGS. 1-3) to initially fix the screw 24 at a desired angular position relatively to the body 12. The screw 24 becomes angularly movable relatively to the body 12 when the bioresorbable layer, or a portion thereof, is absorbed as described in detail below.

Outer surface 46 may be smooth, as shown in FIGS. 4-6 and may comprise a cylindrical surface 48 (FIG. 4), a conical surface 50 (FIG. 5) or a spherical surface 52, shown in FIG. 6. Other surface shapes are also feasible. The smooth outer surface 46 may engage the body through frictional contact to fix the angular position of the screw, or external screw threads may be cut into the outer surface 46 upon contact between the outer surface 46 and the body 12 as explained below.

As shown in FIG. 7, the outer surface 46 may have external helical screw threads 54 which are compatible with internal screw threads in holes 16 of the body 12 to effect angular fixation of the screw 24 relative to the body 12. Threads 54 may have the same or different pitch from threads 39 on the shaft 32. Threaded outer surface 46 may comprise a cylindrical surface 56 as shown in FIG. 7, a conical surface 58 as shown in FIG. 8, or a spherical surface 60 as shown in FIG. 9.

Figure 11:
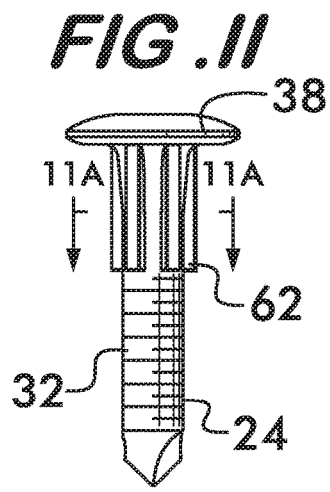
Figure 11A:
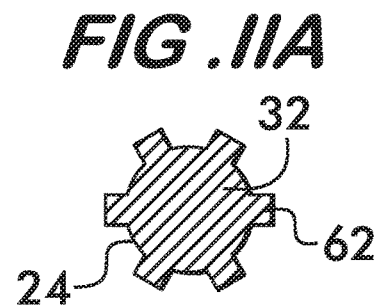
Figure 12:
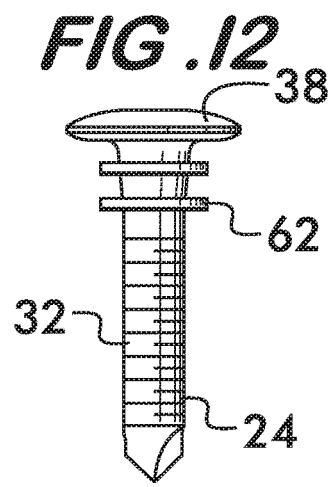
Figure 13:
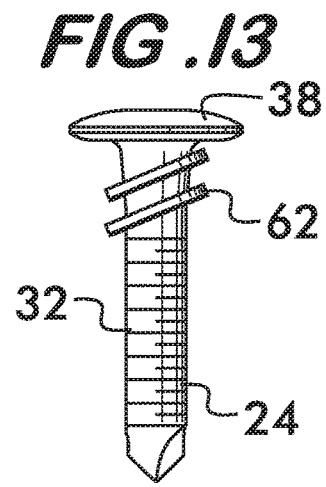

To facilitate attachment of the bioresorbable layer 44 to the shaft 32 of the bone screw 24, surface features may be positioned on a portion of the shaft adjacent to head 38. The surface features increase the surface area of the shaft to afford greater adhesion between the layer 44 and the shaft 32, and also act as positive areas of contact which prevent relative rotation between the layer and the shaft. Examples of shaft surface features are shown in FIGS. 10-13. FIG. 10 shows a screw 24 having the external threads 39 extending along the entire length of shaft 32. FIGS. 11 and 11A show a screw 24 having a plurality of ribs 62 projecting radially outwardly from the shaft 32. In this embodiment, ribs 62 extend lengthwise along the shaft 32. In another embodiment, shown in FIG. 12, the ribs 62 extend circumferentially around the shaft 32. FIG. 13 shows an embodiment wherein the ribs are oriented helically around shaft 32.

Figure 14:
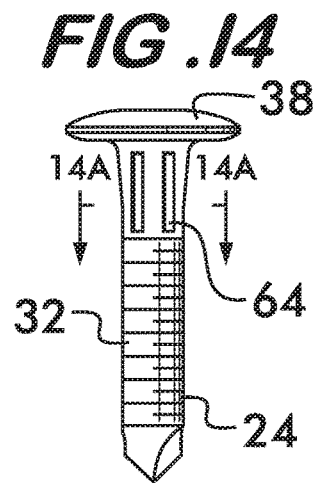
Figure 14A:
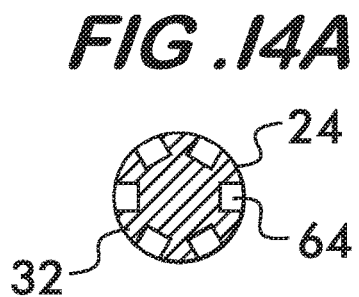
Figure 15:
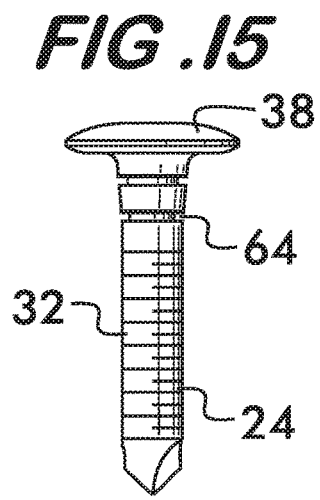
Figure 16:
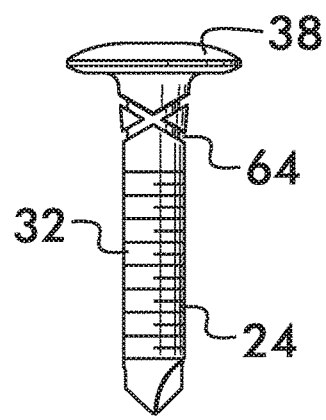
Figure 48:
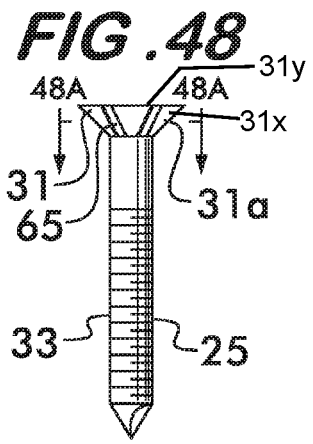

Alternately, as shown in FIGS. 14-16, the surface feature may comprise grooves or channels 64. The channels 64 may extend lengthwise along the shaft 32 as shown in FIG. 14, also shown in cross section in FIG. 14A, or circumferentially around the shaft as shown in FIG. 15, or the channels may be arranged in a helical pattern as shown in FIG. 16. Although shown elsewhere as well, it should be noted that each bone screw head 31 has a top side 31y and a bottom side 31x, and as shown in FIG. 48, the channels 65 extend therebetween.

Additional surface features to facilitate attachment of the bioresorbable layer 44 to shaft 32 include knurling 66 as shown in FIG. 17 or a rough textured surface 68 as shown in FIG. 18. The rough textured surface 68 may result from a powdered metal coating adhered to the shaft using epoxy, cyanoacrylate, or other adhesives, or may be formed by sand blasting the shaft 32. FIG. 19 shows a shaft 32 having a reversed tapered portion 70 adjacent to head 38. Attachment of the bioabsorbable layer may also be facilitated by modifying the cross sectional shape of the shaft 32 over a portion of the proximal end 36 near the head 38. FIGS. 20 and 20A show a shaft 32 with an oval cross section, whereas FIGS. 21 and 21A show a shaft having a polygonal cross section.

FIG. 22 shows an example pin 26, comprising a shaft 72, the shaft having a distal end 74 and an oppositely disposed proximal end 76 to which a head 78 is attached. The pin 26 may be cannulated, having a duct 80 therethrough. In this embodiment, a layer of bioresorbable material 44 is positioned surrounding a portion 82 of the shaft 72 adjacent to the head 78. The layer of bioresorbable material may be formed on the shaft 72 by injection molding techniques for example. The layer of bioresorbable material 44 has an outer surface 84 which is engageable with the body 12 of the device 10 (see FIGS. 1-3) to initially fix the pin 26 at a desired angular position relatively to the body 12. The pin 26 becomes angularly movable relatively to the body 12 when the bioresorbable layer, or a portion thereof, is absorbed as described in detail below.

Figure 23:
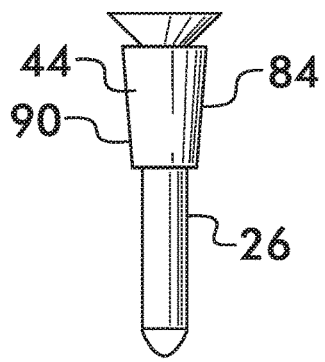
Figure 24:
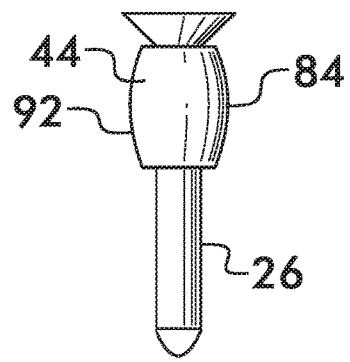

Outer surface 84 may be smooth, as shown in FIGS. 22-24 and may comprise a cylindrical surface 88 (FIG. 22), a conical surface 90 (FIG. 23) or a spherical surface 92, shown in FIG. 24. Other surface shapes are also feasible. The smooth outer surface 84 may engage the body through frictional contact to fix the angular position of the screw, or external screw threads may be cut into the outer surface 84 upon contact between the outer surface 84 and the body 12 as explained below.

Figure 25:
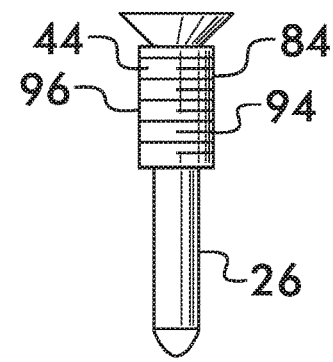
Figure 26:
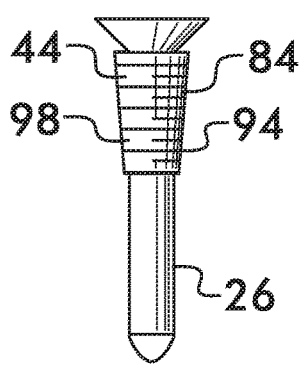
Figure 27:
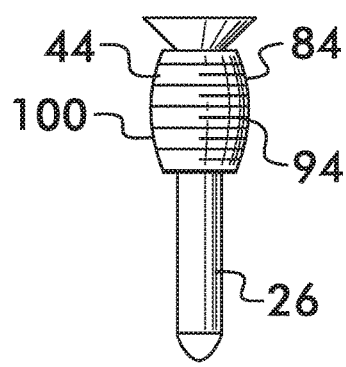

As shown in FIG. 25, the outer surface 84 may have external helical screw threads 94 which are compatible with internal screw threads in holes 16 of the body 12 to effect angular fixation of the pin 26 relative to the body 12. Threaded outer surface 84 may comprise a cylindrical surface 96 as shown in FIG. 25, a conical surface 98 as shown in FIG. 26, or a spherical surface 100 as shown in FIG. 27.

Figure 28:
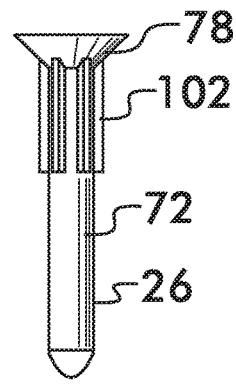
FIGS. 28-31, 31A, 32-38 and 38A are elevational views of pins having features for facilitating attachment of a layer of bioresorbable material thereto.
Figure 29:
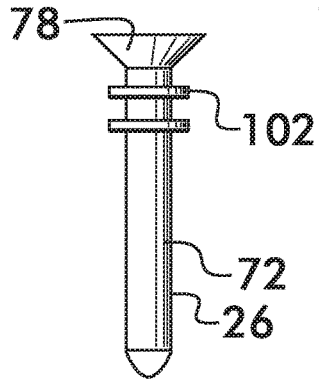
Figure 30:
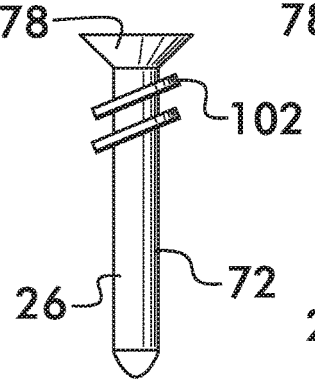

To facilitate attachment of the bioresorbable layer 44 to the shaft 72 of the pin 26, surface features may be positioned on a portion of the shaft adjacent to head 78. The surface features increase the surface area of the shaft to afford greater adhesion between the layer 44 and the shaft 72, and also act as positive areas of contact which prevent relative rotation between the layer and the shaft. Examples of shaft surface features are shown in FIGS. 28-30. FIG. 28 shows a pin 26 having a plurality of ribs 102 projecting radially outwardly from the shaft 72. In this embodiment, ribs 102 extend lengthwise along the shaft 72. In another embodiment, shown in FIG. 29, the ribs 102 extend circumferentially around the shaft 72.

FIG. 30 shows an embodiment wherein the ribs are oriented helically around shaft 72.

Figure 31:
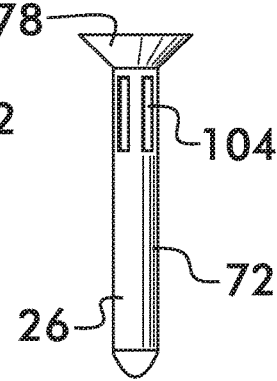
Figure 31A:
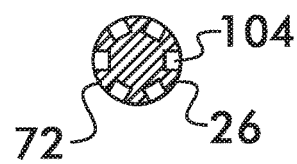
Figure 32:
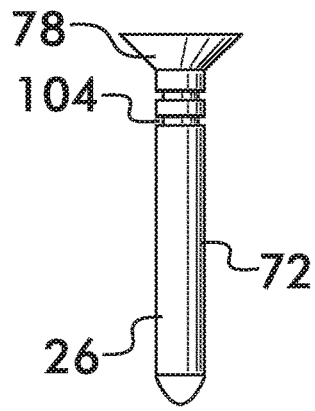
Figure 33:
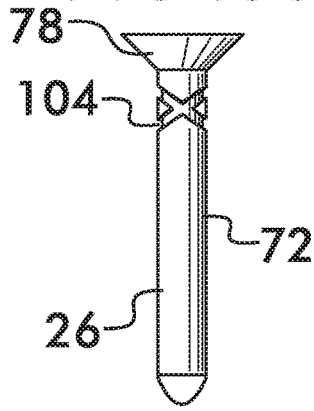

Alternately, as shown in FIGS. 31-33, the surface feature may comprise grooves or channels 104. The channels 104 may extend lengthwise along the shaft 72 as shown in FIG. 31, also shown in cross section in FIG. 31A, or circumferentially around the shaft as shown in FIG. 32, or the channels may be arranged in a helical pattern as shown in FIG. 33.

Figure 34:
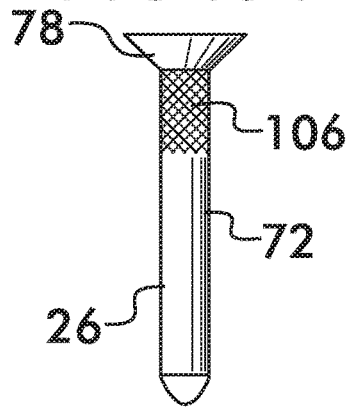
Figure 35:
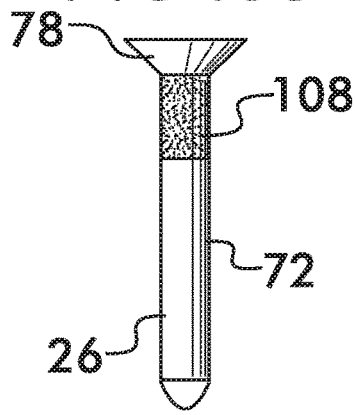
Figure 36:
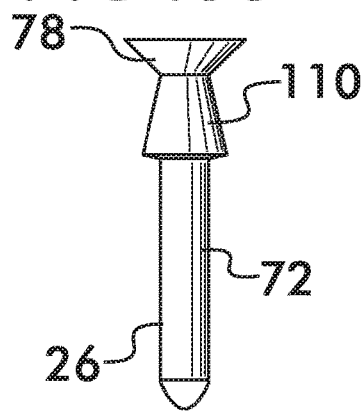
Figure 37:
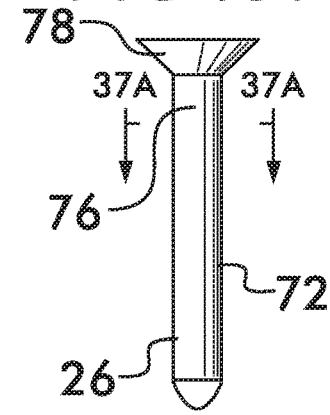
Figure 37A:
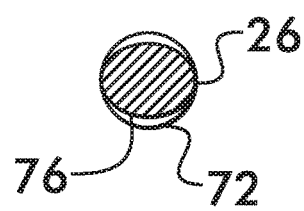
Figure 38:
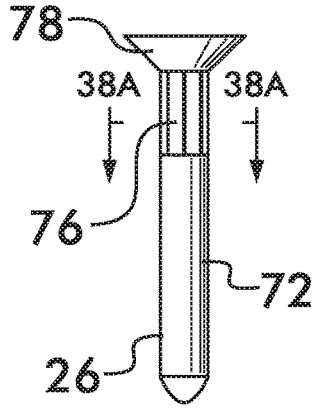
Figure 38A:
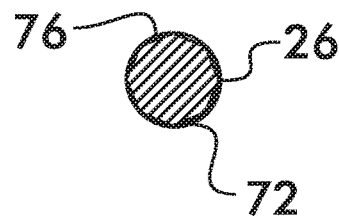

Additional surface features to facilitate attachment of the bioresorbable layer 44 to shaft 72 include knurling 106 as shown in FIG. 34 or a rough textured surface 108 as shown in FIG. 35. The rough textured surface 108 may result from a powdered metal coating adhered to the shaft using epoxy, cyanoacrylate, or other adhesives, or may be formed by sand blasting the shaft 72. FIG. 36 shows a shaft 72 having a reversed tapered portion 110 adjacent to head 78. Attachment of the bioabsorbable layer may also be facilitated by modifying the cross-sectional shape of the shaft 72 over a portion of the proximal end 76 near the head 78. FIGS. 37 and 37A show a shaft 32 with an oval cross section, whereas FIGS. 38 and 38A show a shaft having a polygonal cross section.

Figure 39:
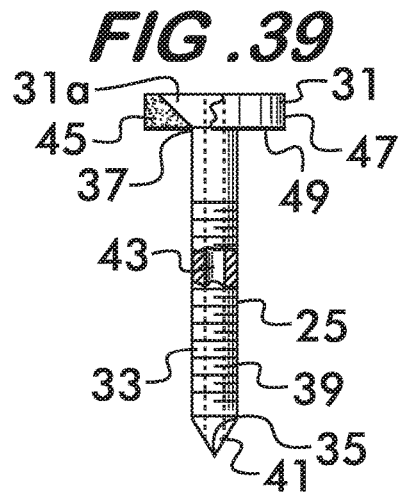
FIGS. 39-44 are partial sectional views of bone screws having a layer of bioresorbable material thereon.

FIG. 39 shows another example bone screw 25, comprising a shaft 33, the shaft having a distal end 35 and an oppositely disposed proximal end 37 to which a head 31 is attached. Head 31 has a surface portion 31a contiguous with the proximal end 37 of shaft 33. Shaft 33 has external helical screw threads 39 extending along at least a portion of the shaft.

Cutting flutes 41 may be positioned at the distal end 35 of the shaft 33, and the screw 25 may be cannulated, having a duct 43 therethrough. In this embodiment, a layer of bioresorbable material 45 is positioned surrounding the surface portion 31a of head 31 contiguous with the proximal end 37 of shaft 33. The layer of bioresorbable material may be formed on the head 31 by injection molding techniques for example. The layer of bioresorbable material 45 has an outer surface 47 which is engageable with the body 12 of the device 10 (see FIGS. 1-3) to initially fix the screw 25 at a desired angular position relatively to the body 12. The screw 25 becomes angularly movable relatively to the body 12 when the bioresorbable layer, or a portion thereof, is absorbed as described in detail below.

Figure 40:
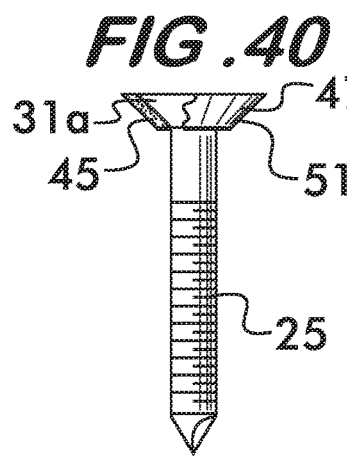
Figure 41:
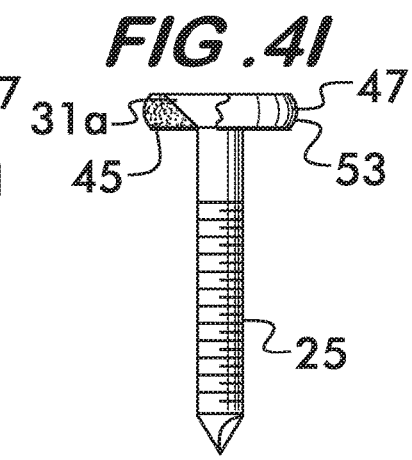

Outer surface 47 may be smooth, as shown in FIGS. 39-41 and may comprise a cylindrical surface 49 (FIG. 39), a conical surface 51 (FIG. 40) or a spherical surface 53, shown in FIG. 41. Other surface shapes are also feasible. The smooth outer surface 47 may engage the body through frictional contact to fix the angular position of the screw, or external screw threads may be cut into the outer surface 47 upon contact between the outer surface 47 and the body 12 as explained below.

Figure 42:
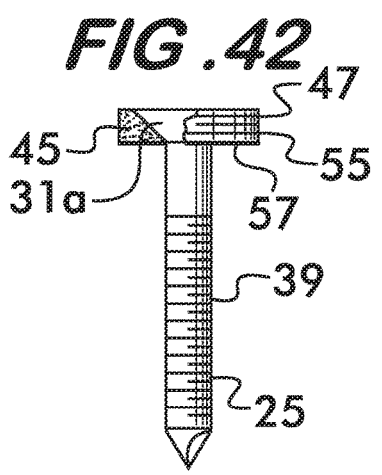
Figure 43:
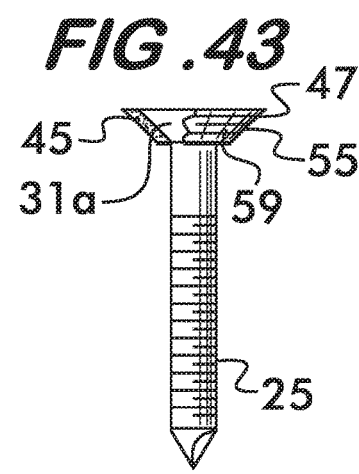
Figure 44:
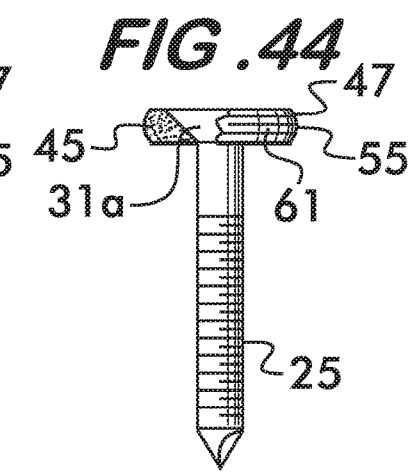

As shown in FIG. 42, the outer surface 47 may have external helical screw threads 55 which are compatible with internal screw threads in holes 16 of the body 12 to effect angular fixation of the screw 25 relative to the body 12. Threads 55 may have the same or different pitch from threads 39 on the shaft 33. Threaded outer surface 47 may comprise a cylindrical surface 57 as shown in FIG. 42, a conical surface 59 as shown in FIG. 43, or a spherical surface 61 as shown in FIG. 44.

To facilitate attachment of the bioresorbable layer 45 to the shaft 33 of the bone screw 25, surface features may be positioned on the surface 31a of head 31 contiguous with the proximal end 37 of shaft 33. The surface features increase the surface area of the head to afford greater adhesion between the layer 45 and the head 31, and also act as positive areas of contact which prevent relative rotation between the layer and the head.

Figure 45:
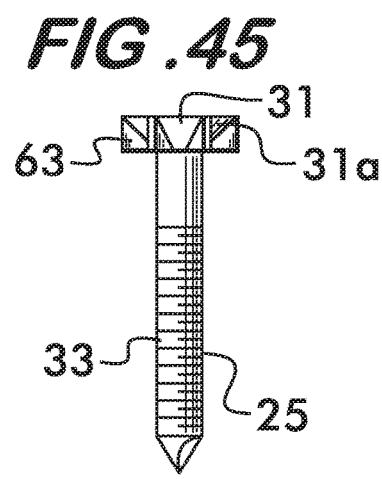
FIGS. 45-48, 48A, 49-53, 53A, 54 and 54A are detailed elevational views of bone screws having features for facilitating attachment of a layer of bioresorbable material thereto.
Figure 46:
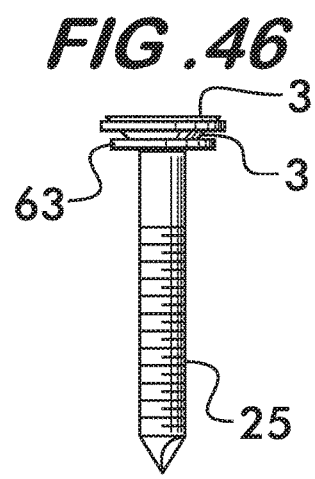
Figure 47:
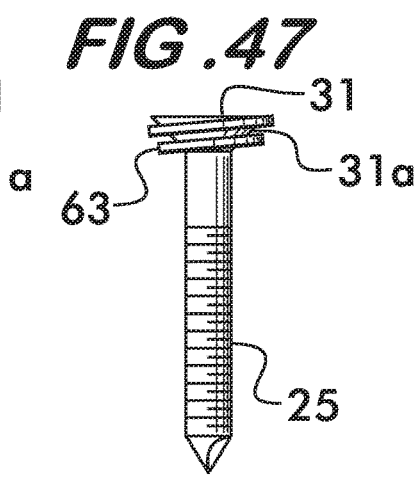

Examples of head surface features are shown in FIGS. 45-47. FIG. 45 shows a screw 25 having a plurality of ribs 63 projecting radially outwardly from the head 31. In this embodiment, ribs 63 extend toward the shaft 33. In another embodiment, shown in FIG. 46, the ribs 63 extend circumferentially around the head 31. FIG. 47 shows an embodiment wherein the ribs are oriented helically around head 31.

Figure 48A:
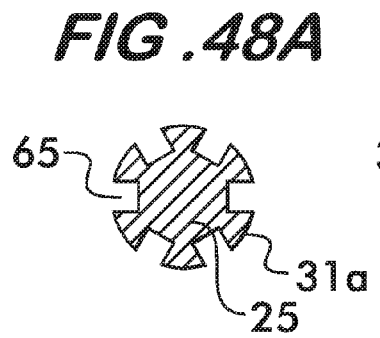
Figure 49:
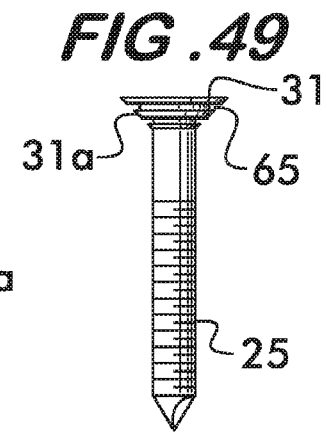
Figure 50:
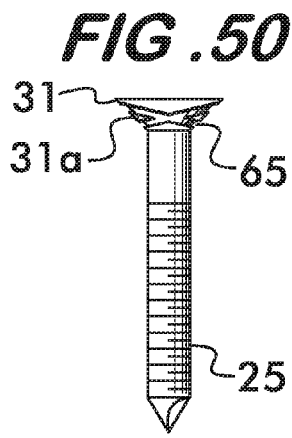

Alternately, as shown in FIGS. 48-50, the surface feature may comprise grooves or channels 65. The channels 65 may extend toward the shaft 33 as shown in FIG. 48, also shown in cross section in FIG. 48A, or circumferentially around the shaft as shown in FIG. 49, or the channels 65 may be arranged in a helical pattern as shown in FIG. 50.

Figure 51:
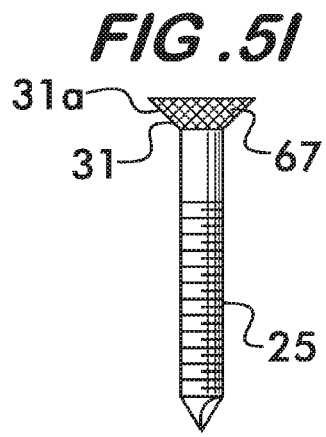
Figure 52:
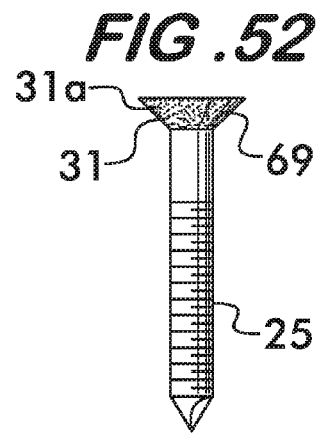
Figure 53:
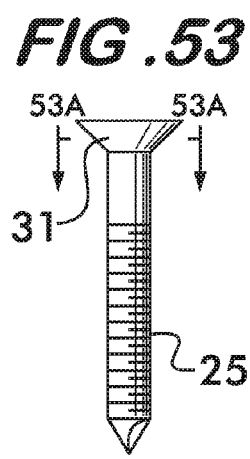
Figure 53A:
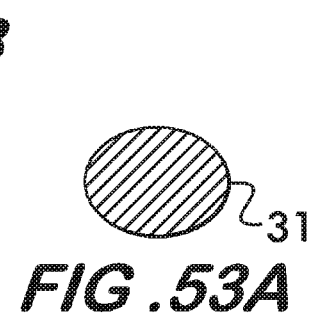
Figure 54:
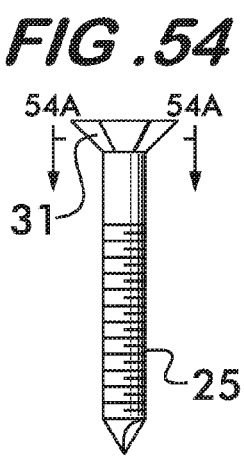
Figure 54A:
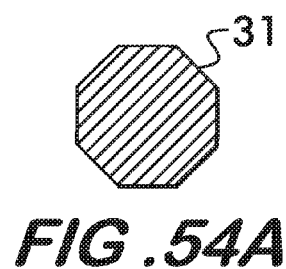

Additional surface features to facilitate attachment of the bioresorbable layer 45 to head 31 include knurling 67 as shown in FIG. 51 or a rough textured surface 69 as shown in FIG. 52. The rough textured surface 69 may result from a powdered metal coating adhered to the shaft using epoxy, cyanoacrylate, or other adhesives, or may be formed by sand blasting the shaft 33. Attachment of the bioabsorbable layer may also be facilitated by modifying the cross sectional shape of the head 31. FIGS. 53 and 53A show a head 31 with an oval cross section, whereas FIGS. 54 and 54A show a head 31 having a polygonal cross section.

FIG. 55 shows an example pin 27, comprising a shaft 73, the shaft having a distal end 75 and an oppositely disposed proximal end 77 to which a head 79 is attached. Head 79 has a surface portion 79a contiguous with the proximal end 77 of shaft 73. The pin 27 may be cannulated, having a duct 81 therethrough. In this embodiment, a layer of bioresorbable material 45 is positioned surrounding the surface portion 79a of head 79 contiguous with the proximal end 77 of shaft 73. The layer of bioresorbable material may be formed on the head 79 by injection molding techniques for example. The layer of bioresorbable material 45 has an outer surface 85 which is engageable with the body 12 of the device 10 (see FIGS. 1-3) to initially fix the pin 27 at a desired angular position relatively to the body 12. The pin 27 becomes angularly movable relatively to the body 12 when the bioresorable layer, or a portion thereof, is absorbed as described in detail below.

Outer surface 85 may be smooth, as shown in FIGS. 55-57 and may comprise a cylindrical surface 89 (FIG. 55), a conical surface 91 (FIG. 56) or a spherical surface 93, shown in FIG. 57. Other surface shapes are also feasible. The smooth outer surface 85 may engage the body through frictional contact to fix the angular position of the screw, or external screw threads may be cut into the outer surface 85 upon contact between the outer surface 85 and the body 12 as explained below.

As shown in FIG. 58, the outer surface 85 may have external helical screw threads 95 which are compatible with internal screw threads in holes 16 of the body 12 to effect angular fixation of the pin 27 relative to the body 12. Threaded outer surface 85 may comprise a cylindrical surface 97 as shown in FIG. 58, a conical surface 99 as shown in FIG. 59, or a spherical surface 101 as shown in FIG. 60.

To facilitate attachment of the bioresorbable layer 45 to the head 79 of the pin 27, surface features may be positioned on the surface 79a of the head 79 contiguous with shaft 73. The surface features increase the surface area of the head to afford greater adhesion between the layer 45 and the head 79, and also act as positive areas of contact which prevent relative rotation between the layer and the head. Examples of head surface features are shown in FIGS. 61-63. FIG. 61 shows a pin 27 having a plurality of ribs 103 projecting radially outwardly from the head 79. In this embodiment, ribs 103 extend toward the shaft 73. In another embodiment, shown in FIG. 62, the ribs 103 extend circumferentially around the head 79. FIG. 63 shows an embodiment wherein the ribs 103 are oriented helically around head 79.

Alternately, as shown in FIGS. 64-66, the surface feature may comprise grooves or channels 105 on head 79. The channels 105 may extend toward the shaft 73 as shown in FIG. 64, also shown in cross section in FIG. 64A, or circumferentially around the head as shown in FIG. 65, or the channels 105 may be arranged in a helical pattern as shown in FIG. 66.

Additional surface features to facilitate attachment of the bioresorbable layer 45 to head 79 include knurling 107 as shown in FIG. 67 or a rough textured surface 109 applied to the head as shown in FIG. 68. The rough textured surface 109 may result from a powdered metal coating adhered to the shaft using epoxy, cyanoacrylate, or other adhesives, or may be formed by sand blasting the head 79. Attachment of the bioabsorbable layer may also be facilitated by modifying the cross sectional shape of the head 79.

FIGS. 69 and 69A show a head 79 with an oval cross section, whereas FIGS. 70 and 70A show a head having a polygonal cross section.

Figure 71:
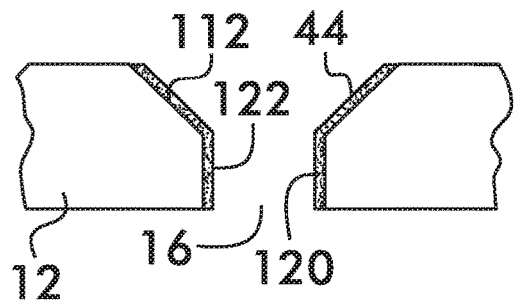
FIGS. 71, 71A, 72, 72A, 73, 73A, 74 and 74A are partial sectional views of a portion of a fixation device having a bioresorbable layer thereon.
Figure 71A:
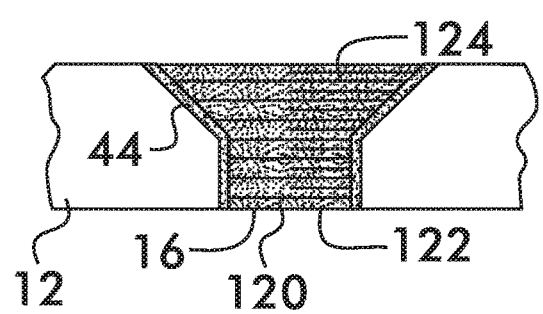
Figure 72:
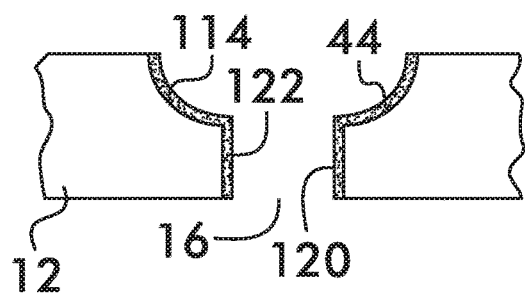
Figure 72A:
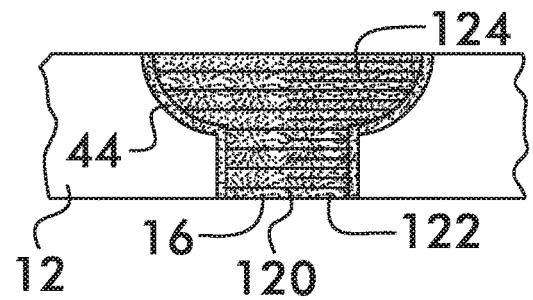
Figure 73:
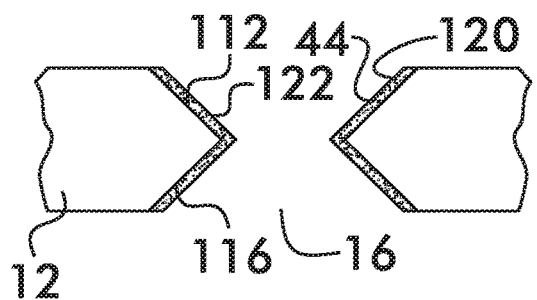
Figure 73A:
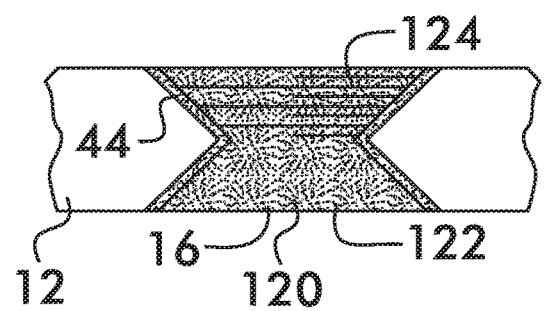
Figure 74:
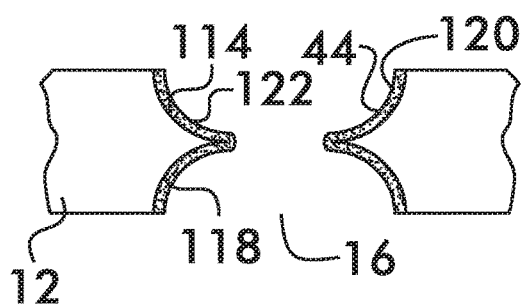
Figure 74A:
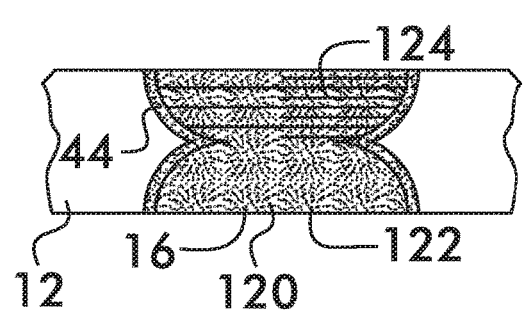

FIGS. 71-74 show detailed cross sectional views of alternate embodiments of holes 16 in body 12, which represent, for example, the holes through bone plate 14, shown in FIG. 1, hip screw 28, shown in FIG. 2, and intramedullary rod 30, shown in FIG. 3. FIG. 71 shows hole 16 in body 12 having a countersink surface 112 surrounding hole 16. The countersink hole in this example is conical. FIG. 72 shows a spherical countersink surface 114. The countersink surfaces 112 and 114 permit angular motion of the fasteners 18 relative to the body 12 when the fasteners are released from the body by absorbtion of the bioresorbable material as described below. The range of angular motion of the fasteners is further augmented by the use of an undercut surface 116 in conjunction with the countersink surface as shown in FIG. 73. Undercut surface 116 is positioned opposite to the countersink surface, meaning that the undercut surface is positioned surrounding the hole 16 on an opposite face of the body 12. FIG. 73 shows a conical undercut surface 116 matched with a conical countersink surface 112, while FIG. 74 illustrates a spherical undercut surface 118 matched with a spherical countersink surface 114.

Figure 75:
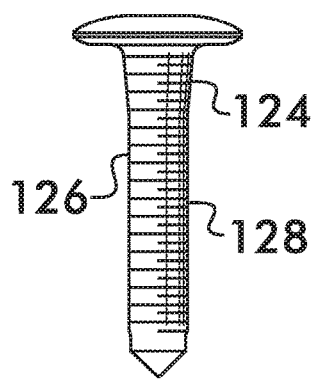
FIGS. 75-77 are elevational views of fasteners used with the fixation device.
Figure 76:
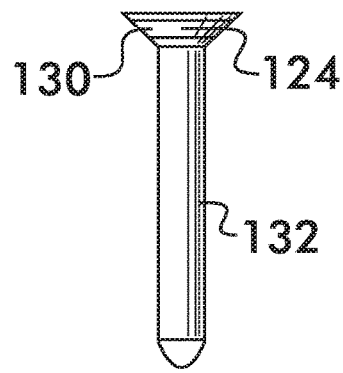
Figure 77:
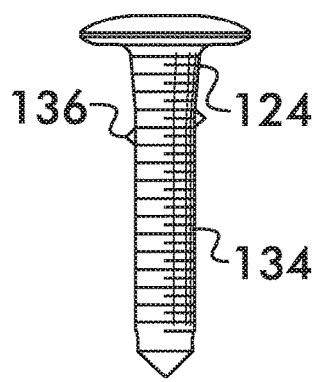

In the embodiment shown in FIG. 71, a layer of bioresorbable material 44 may be positioned on the body 12 within at least one of the holes 16. The layer 44 takes the form of an annulus 120 and has an inwardly facing surface 122 which may be cylindrical and/or conical as shown in FIGS. 71 and 73, as well as spherical, as shown in FIG. 72 and other shapes are also feasible. Inwardly facing surface 122 may be smooth as shown in FIGS. 71-74, or may have internal screw threads 124 as shown in FIGS. 71A-74A. When surface 122 is threaded, the threads engage external threads 124 which are positioned on shaft 126 adjacent to the head of a fastener 128 as shown in FIG. 75, or on a head 130 of a fastener 132 as illustrated in FIG. 76. Note that either or both fasteners 128 and 132 may be a bone screw (FIG. 75) or a pin (FIG. 76). When the inwardly facing surface 122 is smooth it engages fasteners through friction, or, a fastener 134, shown in FIG. 77, may have a cutting edge 136 which cuts internal screw threads into the smooth inwardly facing surface 122 as the fastener is rotated. Again, fastener 134 may be a bone screw or a pin, a bone screw being shown by way of example. It is further understood that fasteners having a layer of bioresorbable material thereon, as shown in FIGS. 4-9, 22-27, 39-44, and 55-60 may also be used with a body having bioresorbable material as shown in FIGS. 71-74 and 71A-74A.

FIGS. 78-83 illustrate operation of the fixation device according to the invention. These figures represent a body 12 having holes 16 that receive fasteners 18. The body could be, for example, part of a bone plate as shown in FIG. 1, a hip screw as shown in FIG. 2, an intramedullary rod as shown in FIG. 3, or another fixation device. The fasteners are bone screws and pins as described above.

Figure 78:
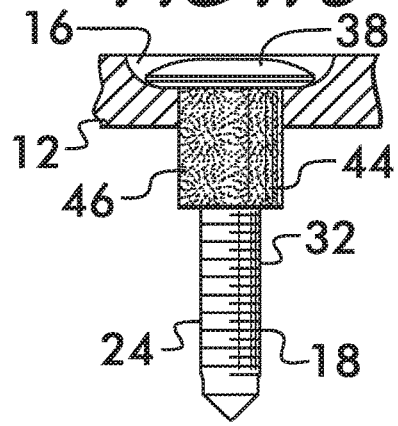
Figure 78A:
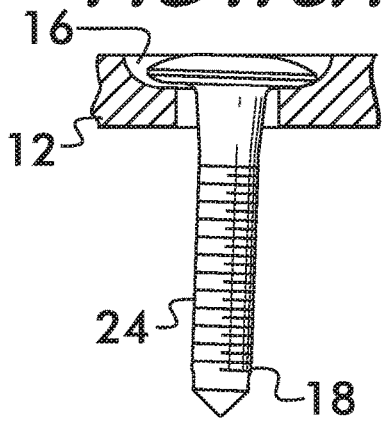

FIG. 78 shows bone screw 24 having the bioresorbable layer 44 on a portion of screw shaft 32 adjacent to the head 38. When the screw 24 is inserted through the hole 16 in body 12 and tightened, the outer surface 46 of the layer 44 engages the body and rigidly fixes the angular orientation of the screw relative to the body (the threaded portion of shaft 32 engages the bone, not shown for clarity). Engagement between the layer 44 and the body 12 may be through any of the example mechanisms described above. For example, outer surface 46 may have external screw threads that engage compatible internal screw threads within hole 16; the outer surface 46 may be smooth and a cutting edge (not shown) positioned within hole 16 cuts external threads in the layer 44; or, the outer surface 46 of layer 44 may depend on friction between the it and the body portion surrounding the hole to provide the desired angular fixation. When all, or at least a portion, of the layer 44 is resorbed, as shown in FIG. 78A, the screw 24 is free to move angularly relatively to the body 12, as evidenced by the canted position shown, and thus the interaction between the body 12 and the bone is transformed from a region of rigid fixation to a region of flexible osteosynthesis which permits micromotion across a fracture site stimulating callous formation and bony healing. Angular rigidity of the screw may be augmented by the particular shape of the layer 44, for example, a conical, tapered shape being advantageous for rigidity. Angular motion of the screw 24 is further controlled through the use of countersink and undercut surfaces as described above and shown in FIGS. 71-74.

Figure 79:
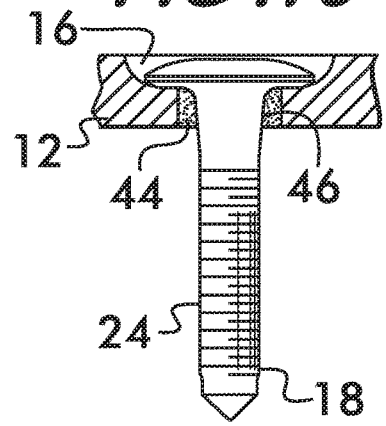

In an alternate embodiment, shown in FIG. 79, the layer of bioresorbable material 44 is positioned on the body 12 within at least one of the holes 16.

When the screw 24 is inserted through the hole 16 in body 12 and tightened, the outer surface 46 of the layer 44 engages the screw and rigidly fixes the angular orientation of the screw relative to the body.

Figure 79A:
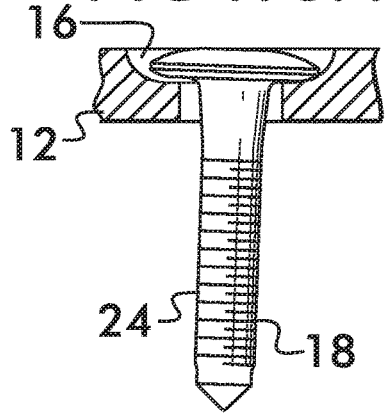

Engagement between the layer 44 and the screw may be through any of the example mechanisms described above. For example, outer surface 46 may have internal screw threads that engage compatible external screw threads on the screw 24; the outer surface 46 may be smooth and a cutting edge (as shown at 136 in FIG. 77) positioned on the screw 24 cuts internal threads in the layer 44 as the screw is rotated, the internal threads engaging external threads on the screw; or, the outer surface 46 of layer 44 may depend on friction between it and the screw shaft to provide the desired angular fixation. When all, or at least a portion, of the layer 44 is resorbed, as shown in FIG. 79A, the screw 24 is free to move angularly relatively to the body 12 and thus transform the engagement between body and bone from a region of rigid fixation to a region of flexible osteosynthesis and permit micromotion across a fracture site stimulating callous formation and bony healing. Angular rigidity of the screw may be augmented by the particular shape of the layer 44, for example, a conical, tapered shape being advantageous for rigidity. Angular motion of the screw 24 is further controlled through the use of countersink and undercut surfaces as described above and shown in FIGS. 71-74.

Figure 80:
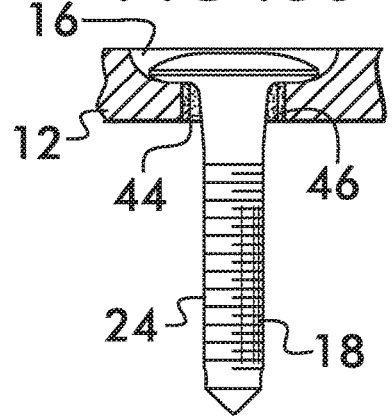
Figure 80A:
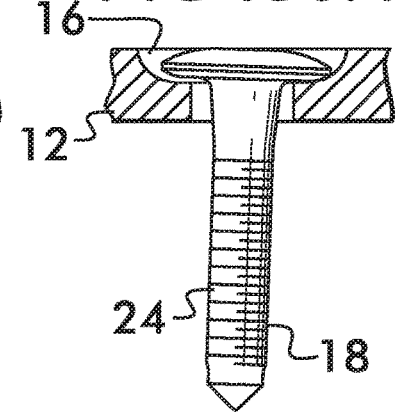

FIGS. 80 and 80A show another embodiment wherein the bioresorbable material layer 44 is positioned on both the screw 24 and the body 12. In this example embodiment, interaction between the outer surfaces 46 of the layers 44 on the screw 24 and on the body 12, as shown in FIG. 80, initially fixes the angular orientation of the screws relatively to the body. Interaction may be through friction between the surfaces or threaded engagement. Countersink and undercut surfaces may again be used to control the limits of relative angular motion between the screw and the body. When the layers 44, or a portion thereof, are resorbed, the screws 24 are no longer rigidly fixed and may move angularly with respect to the body 12 as shown in FIG. 80A, thereby providing the advantages of both the rigid and flexible osteosynthesis systems.

In another embodiment, shown in FIG. 81 a bone screw 25 has the bioresorbable layer 45 on a portion of the head 31. When the screw 25 is inserted through the hole 16 in body 12 and tightened, the outer surface 47 of the layer 45 engages the body and rigidly fixes the angular orientation of the screw relative to the body. Engagement between the layer 45 and the body 12 may be through any of the example mechanisms described above. For example, outer surface 47 may have external screw threads that engage compatible internal screw threads within hole 16; the outer surface 47 may be smooth and a cutting edge (not shown) positioned within hole 16 cuts external threads in the layer 45, or, the outer surface 47 of layer 45 may depend on friction between the it and the body portion surrounding the hole to provide the desired angular fixation. When all, or at least a portion, of the layer 45 is resorbed, as shown in FIG. 81A, the screw 25 is free to move angularly relatively to the body 12 and thus transform from a region of rigid fixation to a region of flexible osteosynthesis and permit micromotion across a fracture site stimulating callous formation and bony healing.

Angular rigidity of the screw may be augmented by the particular shape of the layer 45, for example, a conical, tapered shape as shown being advantageous for rigidity. Angular motion of the screw 25 is further controlled through the use of countersink and undercut surfaces as described above and shown in FIGS. 71-74.

In another alternate embodiment, shown in FIG. 82, the layer of bioresorbable material 45 is positioned on the body 12 within at least one of the holes 16.

When the screw 25 is inserted through the hole 16 in body 12 and tightened, the outer surface 47 of the layer 45 engages the screw's head 31 and rigidly fixes the angular orientation of the screw relative to the body. Engagement between the layer 45 and the screw head 31 may be through any of the example mechanisms described above. For example, outer surface 47 may have internal screw threads that engage compatible external screw threads on the head 31; the outer surface 47 may be smooth and a cutting edge (not shown) positioned on the screw 25 cuts internal threads in the layer 45, or, the outer surface 47 of layer 45 may depend on friction between it and the head to provide the desired angular fixation.

When all, or at least a portion, of the layer 45 is resorbed, as shown in FIG. 82A, the screw 25 is free to move angularly relatively to the body 12 and thus transform from a region of rigid fixation to a region of flexible osteosynthesis and permit micromotion across a fracture site stimulating callous formation and bony healing. Angular rigidity of the screw may be augmented by the particular shape of the layer 45, for example, a conical, tapered shape (shown) being advantageous for rigidity. Angular motion of the screw 25 is further controlled through the use of countersink and undercut surfaces as described above and shown in FIGS. 71-74.

FIGS. 83 and 83A show another embodiment wherein the bioresorbable material layer 45 is positioned on both the head 31 of screw 25 and the body 12. In this example embodiment, interaction between the outer surfaces 47 of the layers 45 on the screw 25 and on the body 12, as shown in FIG. 80, initially fixes the angular orientation of the screws relatively to the body. Interaction may be through friction between the surfaces or threaded engagement. Countersink and undercut surfaces may again be used to control the limits of relative angular motion between the screw and the body. When the layers 45, or a portion thereof, are resorbed, the screws 25 are no longer rigidly fixed and may move angularly with respect to the body 12 as shown in FIG. 83A, thereby providing the advantages of both the rigid and flexible osteosynthesis systems.

Another embodiment is shown in FIGS. 83B and 83C, wherein screw 25 has a head 31 with a substantially smooth side surface 31*a* and a layer of bioresorbable material 45 on the top of the head 31. Bioresorbable layer 45 engages the body 12 using screw threads 95 which mate with compatible internal threads in hole 16 and initially fix the angular orientation of the screw relative to the body. Screw threads 95 may be molded into the bioresorbable layer 45 when it is applied to the screw 25, or the layer 45 may be initially smooth and the threads cut, for example, as the screw is threaded into the hole 16. When the bioresorbable layer 45 is resorbed, as shown in FIG. 83C, the screw 25 no longer fixedly engages the body 12 and is free to rotate angularly relative to the body. Note that a counter sunk screw is shown by way of example, but other shapes of screw heads and bioresorbable layers, such as cylindrical, conical and spherical shapes, are equally feasible.

The invention also encompasses a method of treating a bone fracture in a living organism having a plurality of bone fragments. The method comprises:

- attaching a body to at least two of the bone fragments using a plurality of fasteners joining the body to the fragments;
- fixing an angular orientation of at least one of the fasteners in relation to the body using a bioresorbable material positioned between the fastener and the body, the bioresorbable material contacting the one fastener and the body and preventing relative rotation therebetween;
- allowing the bioresorbable material to be resorbed by the living organism, thereby allowing relative rotation between the one fastener and the body.

The fasteners used in the method according to the invention include bone screws and pins as described herein. The bioresorbable material may be located on the fastener, on the body, or on both the fastener and the body. The angular orientation of the fasteners relative to the body may be fixed by frictional engagement between the body and the bioresorbable layer on the fastener, by frictional engagement between the fastener and the bioresorbable layer on the body, or between bioresorbable layers on both the body and the fastener. The angular orientation of the fasteners relative to the body may be also fixed by engagement between internal screw threads on the body and external screw threads on the bioresorbable layer on the fastener, by engagement between external screw threads on the fastener and internal screw threads on the bioresorbable layer on the body, or between internal and external screw threads on the bioresorbable layers on both the body and the fastener, respectively. The body may be part of a fixation device, such as a bone plate, a hip screw, an intramedullary rod and the like.

FIGS. 84 and 85 show an example body 12 in the form of a bone plate 140 according to the invention. Plate 140 comprises a bone contacting surface 142 (FIG. 85) and an obverse surface 144 (FIG. 84) arranged opposite to the bone contacting surface 142. Side surfaces 146 extend between the bone contacting and obverse surfaces 142 and 144. A plurality of holes 148 extend between the bone contacting surface 142 and the obverse surface 144. Holes 148 receive fasteners 18, which could be bone screws as shown in FIGS. 4-9 and 39-44, and/or pins as shown in FIGS. 22-27, and 55-60 (fastener 18 is shown as a bone screw by way of example). The holes 148 may be round, as well as non-round, for example oval or elliptical as shown in FIGS. 86 and 87. Other, more complicated shapes are also feasible. One or more cutting edges 137 may be positioned in the holes to cut threads in a bioresorbable material layer positioned on the fastener 18 as described above. The holes may also be countersunk and undercut as described above. A layer of bioabsorbable material 44 may be positioned within one or more of the holes 148 similar to the embodiments illustrated in FIGS. 71-74 and 71A-74A.

As best shown in FIGS. 84 and 85, the plate 140 comprises a plurality of channels 150 positioned within either or both the obverse surface 144 and the bone contacting surface 142. Each channel 150 extends from a hole 148 to a side surface 146 and facilitates the flow of bodily fluids to and from the hole. This flow of fluids allows bioresorbable layers 44, either on the plate 140 or the fasteners 18, or on both, to be readily resorbed to transform the plate 140 from operation as a rigid osteosynthesis device to a flexible osteosynthesis device. When the bioresorbable layers are present, the angular orientation of fasteners 18, which could be bones screws and/or pins as described above, is fixed with respect to the plate 140. When the layers are resorbed the fasteners are free to move angularly with respect to the plate 14 and thereby permit the micromotions conducive to callous formation and bony healing.

Channels 150 as shown in FIGS. 84 and 85 comprise a concave, conical surface. Note that in the example shown, the width of the channel where it intersects side surface 146 is greater than where the channel intersects the hole 148. Channels 150 may have different cross sectional shapes from those shown in FIG. 85. As shown in FIG. 88, the channel 150 may have a spherical shape; FIG. 89 shows a channel 150 having a "V" cross sectional shape; FIG. 90 shows a channel 150 having a cylindrical or "U" cross sectional shape, and FIG. 91 shows a channel 150 having a trapezoidal cross sectional shape. Other channel shapes are also feasible.

As shown in FIG. 92, the body 12 represented by an example bone plate 152 has a plurality of projections 154 on its bone facing side 156.

Projections 154 act as spacers to stand the plate 152 in spaced relation away from bone to permit bodily fluids to flow to and from holes 158 in the plate to facilitate resorbtion of the bioresorbable material on the plate and/or the fasteners use to attach the plate to the bone. Projections 154 may be integrally formed with the plate or attached thereto as separate components.

Further by way of example applications of the invention, the hip screw 28, shown in FIG. 2 may use a layer of bioabsorbable material 44 surrounding a portion of the shaft adjacent to the head of the compressing screw 24a. As shown in FIG. 3, screw 24, which secures the intramedullary rod 30 to bone portion 20b, may have a layer of bioresorbable material 44 positioned on a portion of the screw shaft in spaced relation away from the head. Pin 26 may also have a layer of bioresorbable material positioned along its shaft as well.

The bioresorbable materials comprising the layers attached to the fasteners, such as the bone screws and pins, as well as the layers on the body, such as the bone plate, the plate associated with the hip screw, and the intramedullary rod may comprise polymer materials and/or polymer-glass/ceramic including (but not limited to) polylactic acid (PLA), poly-L-lactic-co-glycolic acid (PLGA), poly-D/L-lactic acid with or without polyglycolic acid (PDLLA, PDLLA-co-PGA), poly-L-lactic acid with or without -tricalcium phosphate (PLLA, PLLA-TCP), poly-L-lactic acid with hydroxyapatite (PLLA-HA), polycaprolactone (PCL), polycaprolactone-Calcium Phosphate (PCL-CaP), poly(L-lactide-co-D,L-lactide) (PLADLA), hydroxyapatite (HA), tricalcium phosphate (-TCP) and combinations thereof. Nanodiamond particles may be admixed with the bioresorbable materials to increase their strength.

Additionally, bioresorbable materials which expand when in contact with bodily fluids, or by the action of heat or ultrasonic waves may also be feasible for use with the fixation device according to the invention. Such materials include copolymer lactic glycolic acid (80/20), biodegradeable self-expanding poly-L,D-lactide, PDLLA comprising D-Lactide and L-lactide and poly-L-lactide and poly-E-caprolactone homopolymers.

Expanding or swelling polymeric materials include the monomers methylmethacrylate and acrylic acid and cross linking agent allymelhacrylate. Material layers made of these materials swell by absorbtion of body fluids and thereby produce fixation between the fastener and the bone plate, hip screw or intramedullary rod by an interference fit.

Selective degradation of the bioresorbable material layer may be controlled at the discretion of the surgeon or healthcare practitioner through various means including focal hydrolysis with acids, alkalis or enzymes.

Other means of inducing degradation include the exposure of the bioresorbable layer to UV light or radiation, oxidation, high temperatures, ultrasound and focused high intensity acoustic pulses.

What is claimed is:

1. A bone fastener comprising:
a shaft configured for attachment to a bone;
a head attached to the shaft, the head having channels therein; and
a bioresorbable material engaged to the shaft and the head, and extending into the channels, wherein the channels act as positive areas of contact that prevent rotation between the bioresorbable material and the shaft.

2. The bone fastener of claim 1, wherein the shaft includes threads.

3. The bone fastener of claim 1, wherein the head has a top side and a bottom side, and wherein the channels extend between the top side and the bottom side.

4. The bone fastener of claim 1, wherein the head has a top side and a bottom side, and wherein the channels extend through the top side to the bottom side.

5. The bone fastener of claim 1, wherein the head has a top side and a bottom side, and wherein the channels are located on the bottom side of the head.

6. The bone fastener of claim 1, wherein the channels start at a top side of the head and extend to a bottom side of the head.

7. The bone fastener of claim 1, wherein the channels are parallel to the shaft.

8. The bone fastener of claim 1, wherein the channels are perpendicular to the shaft.

9. The bone fastener of claim 1, wherein the channels are at an angle to the shaft.

10. A bone fastener comprising:
a shaft configured for attachment to a bone;
a head having a surface portion contiguous with the shaft; and
a bioresorbable material;
wherein the surface portion contiguous with the shaft has channels that act as a positive area of contact engaged with the bioresorbable material that extends into the channels to prevents rotation of the bioresorbable material relative to the shaft and head during insertion of the bone fastener into a bone.

11. The bone fastener of claim 10, wherein the shaft includes threads.

12. The bone fastener of claim 10, wherein the channels extend between a top side and a bottom side of the head.

13. The bone fastener of claim 12, wherein the channels extend through the top side to the bottom side.

14. The bone fastener of claim 12, wherein the channels are located on the bottom side of the head.

15. The bone fastener of claim 10, wherein the channels are parallel to the shaft.

16. The bone fastener of claim 10, wherein the channels are perpendicular to the shaft.

17. The bone fastener of claim 10 wherein the channels are at an angle to the shaft.

18. The bone fastener of claim 10, wherein the channels start at a top side of the head and extend to a bottom side of the head.

* * * * *